(12) United States Patent
Satake et al.

(10) Patent No.: US 8,986,326 B2
(45) Date of Patent: Mar. 24, 2015

(54) GASPER AND GRASPING TOOL

(75) Inventors: Motoi Satake, Tokyo (JP); Atsushi Ban, Tokyo (JP); Yoshihisa Kaneko, Tokyo (JP); Koh Kimura, Tokyo (JP); Kazuya Sato, Tokyo (JP); Junichi Kogiso, Center Valley, PA (US)

(73) Assignee: Olympus Medical Systems Corp., Tokyo (JP)

( * ) Notice: Subject to any disclaimer, the term of this patent is extended or adjusted under 35 U.S.C. 154(b) by 1053 days.

(21) Appl. No.: 12/020,076

(22) Filed: Jan. 25, 2008

(65) Prior Publication Data

US 2008/0255427 A1    Oct. 16, 2008

Related U.S. Application Data

(60) Provisional application No. 60/897,562, filed on Jan. 26, 2007.

(51) Int. Cl.
*A61B 17/10* (2006.01)
*A61B 17/08* (2006.01)
*A61B 17/28* (2006.01)
(Continued)

(52) U.S. Cl.
CPC .............. *A61B 17/10* (2013.01); *A61B 17/08* (2013.01); *A61B 17/083* (2013.01); *A61B 17/282* (2013.01); *A61B 17/30* (2013.01); *A61B 18/02* (2013.01); *A61B 18/04* (2013.01); *A61B 18/1445* (2013.01); *A61B 2017/00349* (2013.01); *A61B 2017/2926* (2013.01); *A61B 2017/306* (2013.01); *A61B 2018/00291* (2013.01)
USPC .......................................... 606/142; 606/151

(58) Field of Classification Search
USPC .................. 606/142, 151, 155, 156, 157, 143
See application file for complete search history.

(56) References Cited

U.S. PATENT DOCUMENTS

| 4,690,672 | A | | 9/1987 | Veltrup |
| 5,222,961 | A | * | 6/1993 | Nakao et al. .................. 606/143 |

(Continued)

FOREIGN PATENT DOCUMENTS

| JP | 61-68035 A | 4/1986 |
| JP | 2001-120561 A | 5/2001 |

(Continued)

OTHER PUBLICATIONS

Extended Supplementary European Search Report dated Sep. 29, 2010.

(Continued)

*Primary Examiner* — Dianne Dornbusch
*Assistant Examiner* — Alexander Orkin
(74) *Attorney, Agent, or Firm* — Scully, Scott, Murphy & Presser, PC

(57) ABSTRACT

Provided is a grasper including an introduction tube that is capable of being inserted into a body cavity; an operational elongate body that is inserted into the introduction tube so as to advance and retract; and a clip that is attached to a distal end portion of the introduction tube and is operated by the relative movement between the operational elongate body and the introduction tube so as to grasp a body tissue, then is indwelled in a body. The clip has a plurality of grasping arms which are operated to be moved by the operational elongate body or the introduction tube, at least in a direction where the grasping arms are closed, so as to grasp the body tissue; and a retracting portion which retracts a portion of the body tissue between the plurality of grasping arms.

15 Claims, 25 Drawing Sheets

(51) Int. Cl.
*A61B 17/30* (2006.01)
*A61B 18/02* (2006.01)
*A61B 18/04* (2006.01)
*A61B 18/14* (2006.01)
*A61B 17/00* (2006.01)
*A61B 17/29* (2006.01)
*A61B 18/00* (2006.01)

(56) References Cited

U.S. PATENT DOCUMENTS

| | | |
|---|---|---|
| 5,226,908 A | 7/1993 | Yoon |
| 5,792,153 A * | 8/1998 | Swain et al. ............. 606/144 |
| 6,592,596 B1 | 7/2003 | Geitz |
| 7,776,057 B2 * | 8/2010 | Laufer et al. ............. 606/139 |
| 2002/0062130 A1 * | 5/2002 | Jugenheimer et al. ....... 606/142 |
| 2002/0173786 A1 * | 11/2002 | Kortenbach et al. ........... 606/45 |
| 2002/0173805 A1 | 11/2002 | Matsuno et al. |
| 2003/0191365 A1 | 10/2003 | Kobayashi |
| 2003/0195436 A1 | 10/2003 | Van Bladel et al. |
| 2004/0138682 A1 * | 7/2004 | Onuki et al. ............. 606/144 |
| 2004/0194790 A1 * | 10/2004 | Laufer et al. ............. 128/898 |
| 2005/0033312 A1 | 2/2005 | Suzuki |
| 2005/0059985 A1 * | 3/2005 | Kimura ............. 606/151 |
| 2007/0093857 A1 * | 4/2007 | Rogers et al. ............. 606/142 |
| 2008/0234705 A1 * | 9/2008 | Cropper et al. ............. 606/157 |

FOREIGN PATENT DOCUMENTS

| | | |
|---|---|---|
| JP | 2002-112946 | 4/2002 |
| JP | 2002-224124 | 8/2002 |
| JP | 2003-93393 A | 4/2003 |
| JP | 2003-532479 | 11/2003 |
| JP | 2005-21587 | 1/2005 |
| JP | 2005-532479 A | 10/2005 |
| JP | 2006-346341 A | 12/2006 |
| JP | 2007-516731 | 6/2007 |
| WO | WO 2004/008478 A2 | 1/2004 |
| WO | WO 2005/063133 A1 | 7/2005 |

OTHER PUBLICATIONS

Korean Notice of Allowance dated Nov. 20, 2012 from corresponding Korean Patent Application No. 10-2009-7015429, together with an English language translation.

Japanese Office Action dated Jul. 31, 2012 from related Japanese Patent Application No. 2008-555111, together with an English language translation.

* cited by examiner

GASPER AND GRASPING TOOL

Priority is claimed on U.S. patent application Ser. No. 60/897,562 filed on Jan. 26, 2007, the content of which is incorporated herein by reference.

BACKGROUND OF THE INVENTION

1. Field of the Invention

The present invention relates to a grasper and a grasping tool which, for example, arrest bleeding and obstruct an incised portion.

2. Description of Related Art

As an example of a grasper which is inserted into a channel of an endoscope so as to be used for observation through the endoscope, a conventional grasper is disclosed in Japanese Unexamined Patent Application Publication No. 2002-224124. The conventional grasper includes an introduction tube which is inserted into a body cavity; an operational wire which is inserted into the introduction tube so as to advance and retract, and a clip which is detachably attached to a distal end portion of the introduction tube and is operated by the operational wire so as to grasp a body tissue.

In the conventional grasper, the introduction tube is inserted into a body cavity through a channel of an endoscope, and the clip attached to the distal end of the introduction tube is disposed to face a place at which a body tissue is to be grasped, that is, a wound of the body tissue. In this state, while the operational wire is pulled toward an at-hand side, the clip is moved. Then, the distal end of the clip which is biased to spread is closed by a pressing ring attached to the distal end of the introduction tube. Accordingly, the body tissue surrounding the wound of is grasped by the clip, and the clip is indwelled in the body as it is. On the other hand, the introduction tube and the operational wire are drawn out of the body together with the endoscope.

SUMMARY OF THE INVENTION

According to an aspect of the present invention, a grasper includes an introduction tube that is capable of being inserted into a body cavity; an operational elongate body that is inserted into the introduction tube so as to advance and retract; and a grasping tool that is attached to a distal end portion of the introduction tube and is operated by the relative movement between the operational elongate body and the introduction tube so as to grasp a body tissue. The grasping tool has a plurality of grasping arms which are operated to be moved by the operational elongate body or the introduction tube, at least in a direction where the grasping arms are closed, so as to grasp the body tissue; and a retracting portion which retracts a portion of the body tissue between the plurality of grasping arms.

According to another aspect of the invention, a grasper includes an introduction tube that is capable of being inserted into a body cavity; an operational elongate body that is inserted into the introduction tube so as to advance and retract; and a grasping tool that is attached to a distal end portion of the introduction tube and is operated by the relative movement between the operational elongate body and the introduction tube so as to grasp a body tissue. The grasping tool has a plurality of grasping arms which are operated to be closed by the operational elongate body or the introduction tube so as to grasp the body tissue; and a film disposed across the distal end portions of the plurality of grasping arms.

According to a further aspect of the invention, a grasper includes an introduction tube that is capable of being inserted into a body cavity; an operational elongate body that is inserted into the introduction tube so as to advance and retract; and a grasping tool that is attached to a distal end portion of the introduction tube and is operated by the relative movement between the operational elongate body and the introduction tube so as to grasp a body tissue. The grasping tool has a plurality of grasping arms which are operated to be moved by the operational elongate body or the introduction tube at least in a direction where the grasping arms are closed; and a plurality of rotating arms which are rotatably coupled to the distal ends of the respective grasping arms so as to grasp the body tissue.

According to a further aspect of the invention, a grasping tool, which is attached to an introduction tube capable of being inserted into a body cavity and is operated by the relative movement between the introduction tube and an operational elongate body, which is inserted into the introduction tube so as to advance and retract, to grasp a body tissue, includes a plurality of grasping arms that are operated to be closed by the operational elongate body or the introduction tube so as to grasp the body tissue; and a retracting portion that retracts a portion of the body tissue between the plurality of grasping arms.

DETAILED DESCRIPTION OF THE INVENTION

Figure 1:
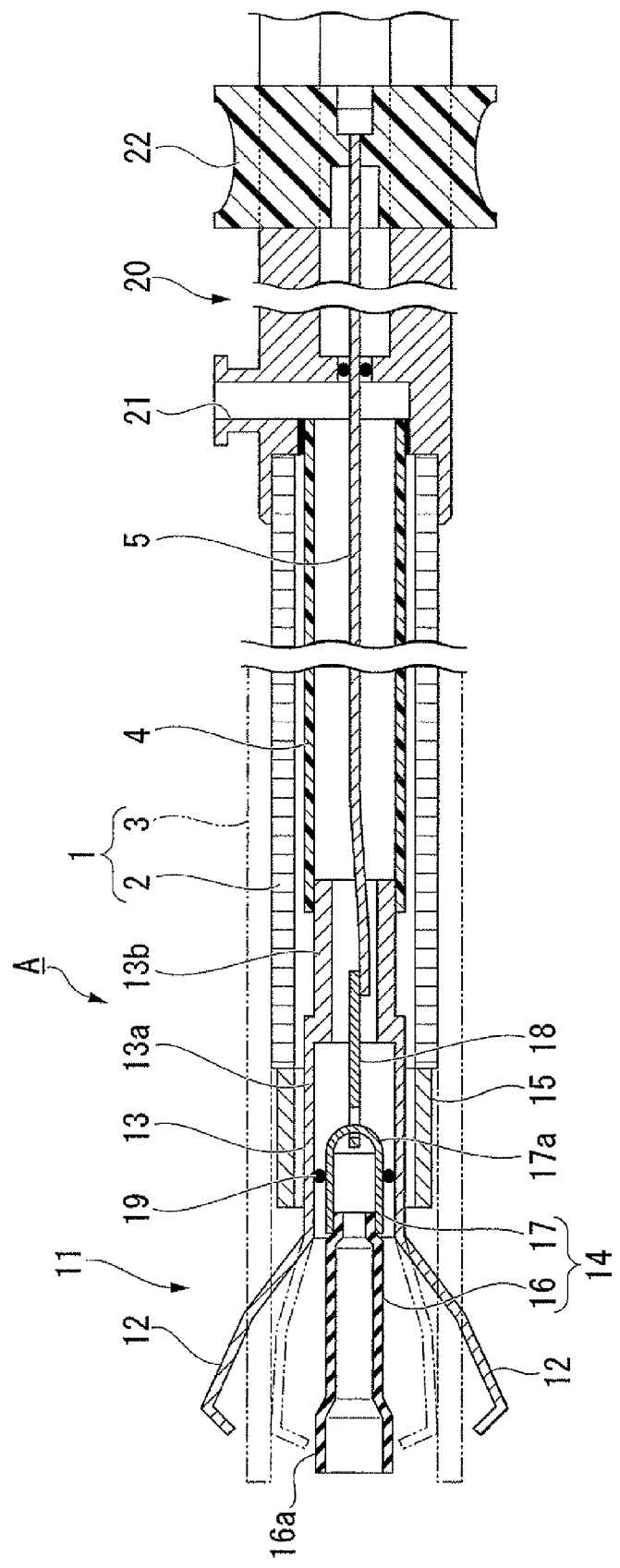
FIG. 1 is a cross-sectional view of a grasper according to a first embodiment of the invention.

Hereinafter, preferred embodiments of the present invention will be described. In the respective embodiments, like reference numerals will be attached to the same components, and duplicated descriptions thereof will be omitted.

[First Embodiment]

Figure 2:
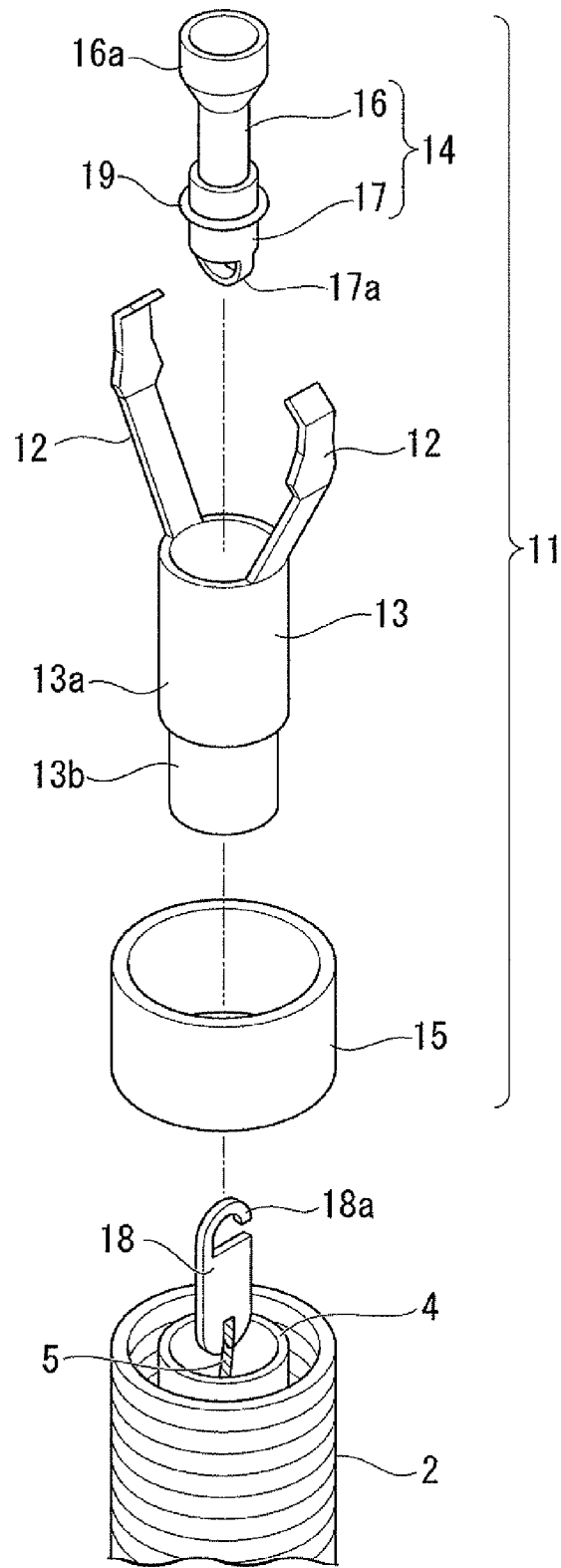
FIG. 2 is a perspective view of essential parts of the grasper according to the first embodiment of the invention.

FIGS. 1 to 20 are diagrams showing a grasper and a clip according to a first embodiment of the invention. FIG. 1 is a cross-sectional view of the grasper according to the first embodiment of the invention. FIG. 2 is a perspective view of essential parts of the grasper according to the first embodiment of the invention. In FIGS. 1 and 2, reference numeral A represents the grasper, and reference numeral 1 represents an introduction tube with flexibility. The introduction tube 1 is inserted into a body cavity through an instrument channel of an endoscope such that the distal end thereof is first inserted. The introduction tube 1 has a coil sheath 2 formed by coiling a wire material and an outer tube 3 which is formed of resin and covers the outer surface of the coil sheath 2. The coil sheath 2 formed by closely coiling a metal wire, for example, has softness as well as flexibility. The outer tube 3 can be moved with respect to the coil sheath 2 in an axial direction thereof. The coil sheath 2 has a suction conduit 4 disposed therein, the suction conduit 4 forming an air passage. The suction conduit 4 is formed of a resin tube with flexibility which is composed of PE (polyethylene), PP (polypropylene), fluorine resin or the like. Inside the suction conduit 4, an operational wire 5 is inserted so as to advance and retract.

The introduction tube 1 has a clip 11 which is detachably attached to the distal end thereof. The clip 11 includes a grasping pipe 13 having a pair of grasping arms 12 integrally formed at the distal end thereof; a suction tube 14 disposed in the grasping pipe 13 so as to move along the axial direction thereof; and a pressing ring 15 which is abutted on the grasping arms 12 so as to inwardly press and close the grasping arms 12, when the grasping pipe 13 is moved toward a proximal end side. In the introduction tube 1, the grasping pipe 13 and so on described in this specification, the left side of FIG. 1 is referred to as a distal end side, and the right side is referred to as a proximal end side.

The grasping arms 12 provided at the distal end of the grasping pipe 13 are biased in an open direction due to their elastic characteristics. The grasping arms 12 are formed of a thin plate material such as stainless steel, Ni—Ti or the like. The grasping pipe 13 with synthetic rigidity has a large-diameter portion 13a formed at the distal end thereof and a small-diameter portion 13b formed at the proximal end side thereof. The grasping arms 12 are formed in the distal end of large-diameter portion 13a. The small-diameter portion 13b is inserted into the distal end of the suction conduit 4 so as to slide along the axial direction.

The suction tube 14 forms a retracting portion which retracts a portion of a body tissue between the grasping arms 12 when the portion of the body tissue is grasped by the grasping arms 12. The suction tube 14 is formed of a soft material so as to be deformed in accordance with the shape of body tissues. Further, the suction tube 14 includes a suction nozzle 16 having a diameter-expanded portion 16a formed at the distal end thereof and a nozzle fixing tube 17 bonded to the proximal end of the suction nozzle 16. Preferably, the suction nozzle 16 is formed of resin which can be deformed in accordance with the shape of body tissues. For example, ethylene vinyl acetate copolymer, low-density polyethylene, silicone, rubber and so on may be used. The nozzle fixing tube 17 has a locked portion 17a formed at the proximal end side thereof, the locked portion 17a being curved in a circular arc shape. The locked portion 17a is locked to a locking portion 18a of a connection plate 18 attached to the distal end of the operational wire 5.

The outer diameter of the suction tube 14 is set to be smaller than the inner diameter of the large-diameter portion 13a of the grasping pipe 13, and is set to be larger than the inner diameter of the small-diameter portion 13b of the grasping pipe 13. Therefore, the suction tube 14 can be relatively displaced inside the large-diameter portion 13a along the axial direction with respect to the large-diameter portion 13a, but cannot be inserted into the small-diameter portion 13b of the grasping pipe 13. When the suction tube 14 is moved toward the proximal end with respect to the small-diameter portion 13b of the grasping pipe 13, the suction tube 14 abuts against the small-diameter portion 13b so as not to be moved. Between the suction tube 14 and the grasping pipe 13, an O-ring 19 for sealing is interposed.

When the clip 11 is assembled to a regular position of the distal end of the introduction tube 1, the distal end of the suction tube 14 slightly projects further than the distal end of the grasping arms 12 (refer to FIG. 1).

When the grasping arms 12 do not grasp a body tissue but are opened, the pressing ring 15 is fitted into the outer circumference of the large-diameter portion 13a of the grasping pipe 13. When the clip 11 is assembled to the distal end of the introduction tube 1, the pressing ring 15 is disposed at the distal end side of the coil sheath 2. Further, as the operational wire 5 is pulled toward the proximal end side, the grasping pipe 13 is moved toward the proximal end side through the suction tube 14. At this time, the pressing ring 15 is moved toward the distal end side with respect to the moved grasping pipe 13 so as to inwardly press the grasping arms 12. Accordingly, the grasping arms 12 are closed. This movement will be described in more detail hereinbelow.

The introduction tube 1 has an operator main body 20 attached to the proximal end thereof. The operator main body 20 has a distal end opening to which the proximal ends of the introduction tube 1 and the suction conduit 4 axe fixed in such a state that they are inserted to the opening. In particular, the suction conduit 4 is inserted and fixed to the distal end opening of the operator main body 20 so as to be maintained in an airtight state. The operator main body 20 has a suction port 21 formed at the distal end thereof the suction port 21 being connected to a suction tube (not shown). Further, the air within the suction conduit 4 is suctioned by a suction source such as a vacuum pump connected to the proximal end side of the suction tube. Further, the operator main body 20 has a slider 22 attached to the middle portion thereof such that the slider 22 can slide along the axial line of the operator main body 20. The proximal end of the operational wire 5 is fixed to the slider 22 by a suitable fixing element such as caulking or the like.

Next, the operation of the grasper constructed in the above-described manner will be described.

First, the endoscope is inserted into a natural opening such as the mouth, anus, or nose of a patient, and a target position is confirmed through an observation device of the endoscope. Then, the grasper A is inserted into the instrument channel of the endoscope.

When the grasper A is delivered as a product from a factory or the like, the distal end of the outer tube 3 projects further than the coil sheath 2 toward the distal end side, as indicated by the dotted and dashed lines of FIG. 1. The grasping arms 12 are housed in the distal end portion of the projecting outer tube 3 in such a state that they are half-opened. In such a state that the grasping arms 12 are housed in the distal end portion of the outer tube 3, the grasper A is inserted into the instrument channel of the endoscope. Then, the distal end of the suction tube 14 or the grasping arms 12 at the distal end of the grasper A is opposed to a bleeding point Pa of a body tissue T1.

Next, by sliding the outer tube 3 on the outer circumference of the coil sheath 2, the outer tube 3 is moved toward the proximal end such that the grasping arms 12 open due to their elastic operation.

While the operator main body 20 is operated, the grasper A is further advanced toward the distal end side such that the distal end of the suction tube 14 is pressed against the bleeding point Pa of the body tissue T1. Inside the suction conduit 4, the air is suctioned by the suction source connected through the suction port 21. Therefore, the bleeding point Pa of the body tissue T1 can be suctioned from the distal end of the suction tube 14 communicating with the suction conduit 4. At this time, tie bleeding point Pa and the body tissue T1 around the bleeding point Pa are pulled, and bleeding from the bleeding point Pa is temporarily arrested.

When the position at which the body tissue T1 is suctioned deviates, the grasper A is moved until the distal end openings of the introduction tube 1 and the suction tube 14 are disposed at a proper position, while the suction continues. However, after the suction is temporarily stopped, the grasper A may be moved.

Figure 3:
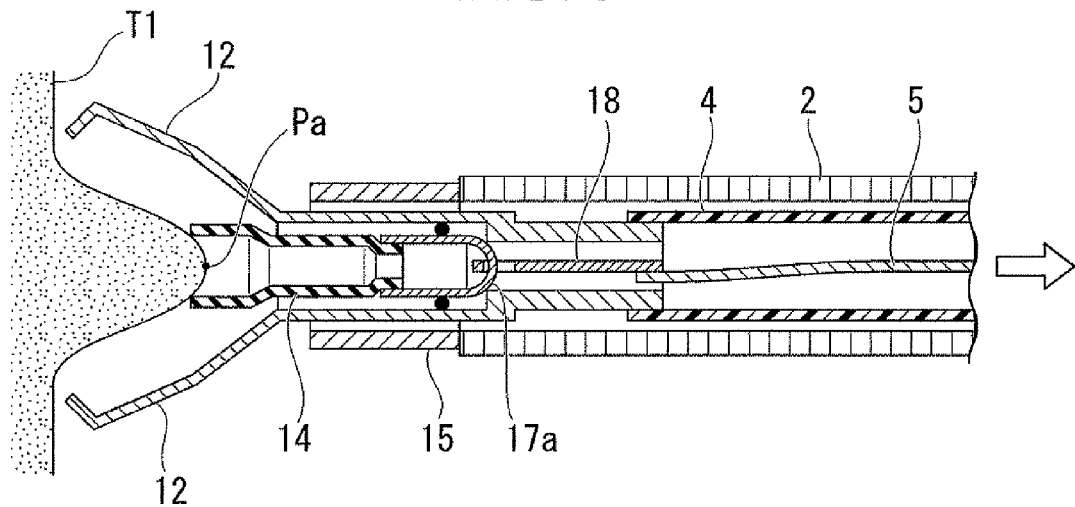
FIG. 3 is a cross-sectional view of essential parts explaining the operation of the grasper according to the first embodiment.
Figure 4:
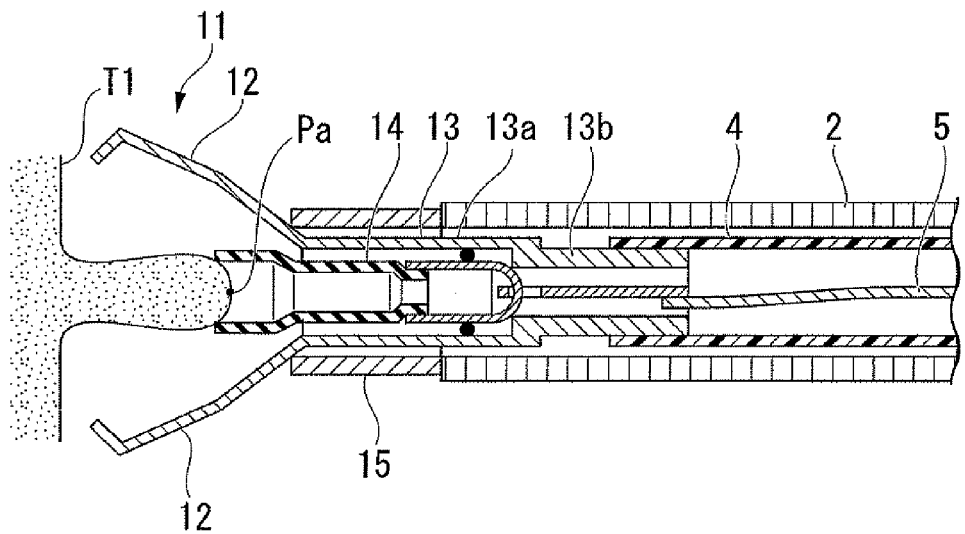
FIG. 4 is a cross-sectional view of essential parts explaining the operation of the grasper according to the first embodiment.

When the grasper A is moved in such a manner that a proper position is suctioned, the slider 22 of the operator main body 20 is moved toward the proximal end, and the suction tube 14 is moved toward the proximal end through the operational wire 5 and the connection plate 18, as shown by an arrow of FIG. 3. When the locked portion 17a at the proximal end side abuts against the distal end of the small-diameter portion 13b of the grasping pipe while the suction tube 14 is moved inside the grasping pipe 13, the suction tube 14 cannot be relatively moved any more. Further, when the suction tube 14 is moved toward the proximal end, the suction tube 14 and the grasping pipe 13 are integrally moved toward the proximal end.

Meanwhile, when the pressing ring 15 abuts against the distal end of the coil sheath 2 of the introduction tube 1, the position thereof is held. Therefore, as the middle portions of the grasping arms 12 are inwardly pressed by the pressing ring 15 which is not moved, the grasping arms 12 are closed. As a result, the body tissue T1 is grasped between the grasping arms 12 such that the portion where the bleeding is temporarily arrested is centered.

Figure 5:
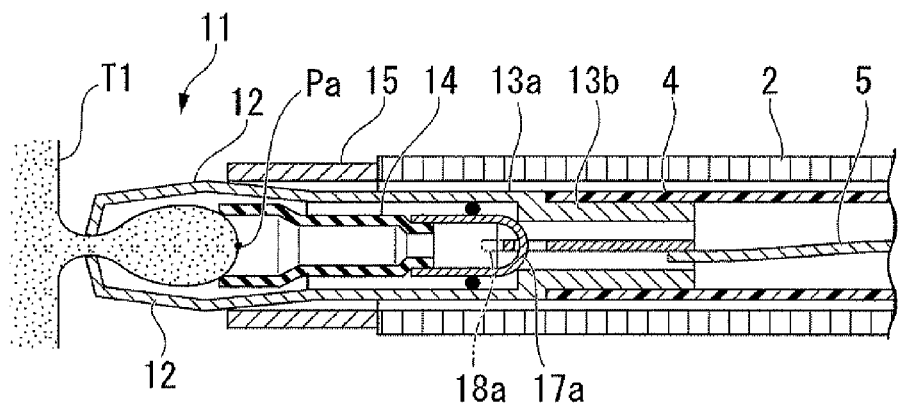
FIG. 5 is a cross-sectional view of essential parts explaining the operation of the grasper according to the first embodiment.

Next, when the slider 22 is further moved toward the proximal end by a strong force, the locking portion 18a of the connection plate 18 is deformed so as to extend, as indicated by dotted and dashed lines of FIG. 5. The locking of the suction tube 14 to the locked portion 17a is released. At this time, since the outer circumference of the grasping arms 12 is pressed by the pressing ring 15, the clip 11 is detached from the operation wire 5 so as to be indwelled in the body of the patient, in a state where the body tissue T1 is grasped.

The strength of the locking portion 18a of the connection plate 18 is set in such a manner that the suction tube 14 can be retracted by the connection plate 18 until it bumps against the small-diameter portion 13b of the grasping pipe 13 and the grasping arms 12 can be then closed while the suction tube 14 and the grasping pipe 13 are integrally moved toward the proximal end. After that, when the suction tube 14 is moved toward the proximal end by a stronger force, the locking portion 18a is plastically deformed so as to extend.

According to the grasper A constructed in the above-described manner, even when it is difficult to find a ligature point because of bleeding, the blood can be suctioned by the suction tube 14 so as to be removed. Therefore, since the ligature point is accurately found, the positioning of the clip 1 is easily performed. Further, since a portion which is being suctioned is clipped, displacement of the body tissue T1 caused by the grasping arms 12 pressing the tissue T1 upon clipping is prevented. As a result, the positioned portion can be accurately ligatured.

Further, since the body tissue T1 is suctioned in a state where the suction tube 14 is set in advance to project further than the grasping arms 12, the grasping arms 12 do not get in the way, and the body tissue T1 can be reliably suctioned. In addition, while the suction state is maintained, the suction tube 14 is previously moved toward the proximal end side so as to be positioned between the pair of grasping arms 12 in advance. The suction tube 14 can be moved to a position wherein the body tissue T1 is easily grasped by the grasping arms 12. Therefore, the body tissue T1 can be reliably ligatured.

The movement of the suction tube 14 toward the proximal end is performed in conjunction with grasping of the body tissue T1 by the grasping arms 12. Therefore, those operations can be carried out by one sequence of operation of simply moving the slider 22 to the proximal end side. As a result, the operations are extremely simplified. Further, since the operating member of the suction tube 14 and that of the clip are the same, it is possible to achieve a reduction in the diameter of the introduction tube 1 such that a suction path is secured.

In the grasper A, as the body tissue T1 is suctioned by the suction tube 14, the body tissue T1 is pulled into the grasping portion of the clip and is then clipped by the grasping arms 12. Therefore, the clip 11 does not need to be strongly pressed against the body tissue T1, and the damage on the neighboring body tissue T1 can be minimized. In particular, a conventional clip which is capable of re-grasping, a point which is to be ligatured may be searched for, while a ligature is temporarily performed. At this time, when a tissue is gripped a number of times, the tissue is easily damaged. In the clip 11, however, only the suction is performed when a ligature point is searched for. Therefore, the damage on the tissue is small.

The grasper A has an advantage in that bleeding is temporarily arrested by the suction prior to the ligature by the grasping arms 12.

In the above-described embodiment, the distal end portion of the outer tube 3 is set to project from the coil sheath 2, and the grasping arms 12 in the projecting distal end portion of the outer tube 3 are held in a half-closed state. Instead of this, the clip 11 may be housed in the introduction tube 1 in advance, and the clip 11 may be then moved toward the distal end through the operational wire by operating the slider such that the grasping arms 12 are opened so as to grasp, when the grasping by the clip 11 is necessary. In this construction, the outer tube 3 can be omitted.

Figure 6:
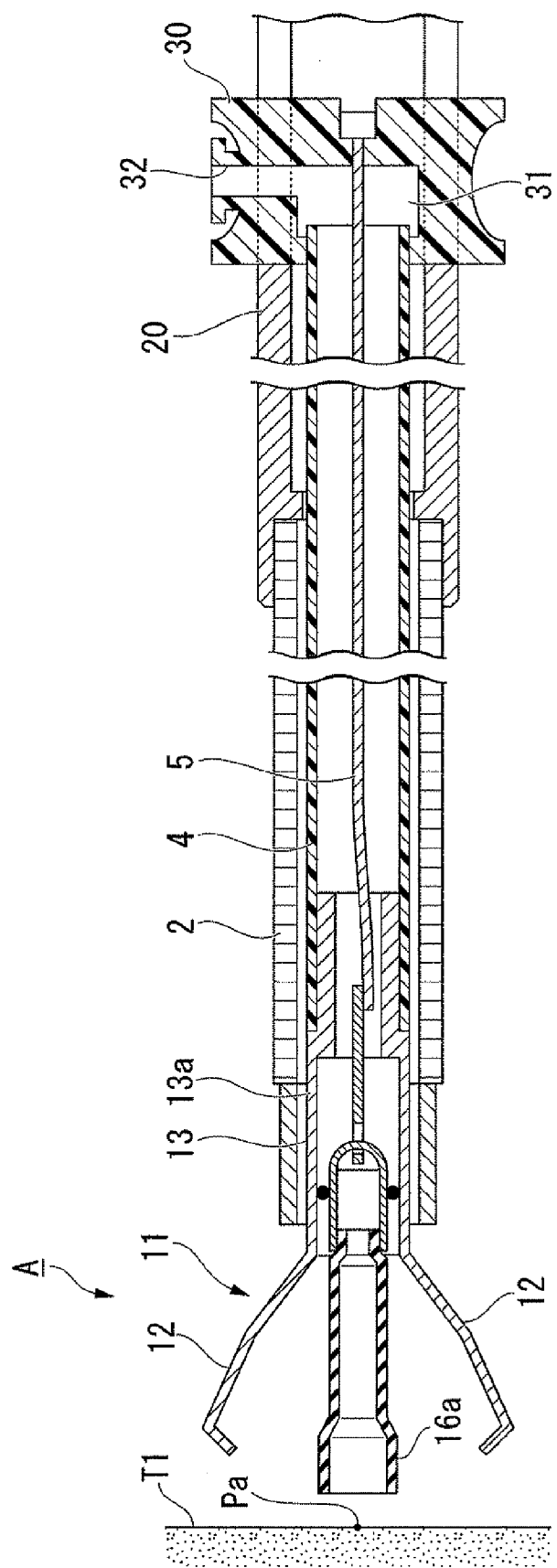
FIG. 6 is a cross-sectional view of a grasper according to a modification of the first embodiment of the invention.
Figure 7:
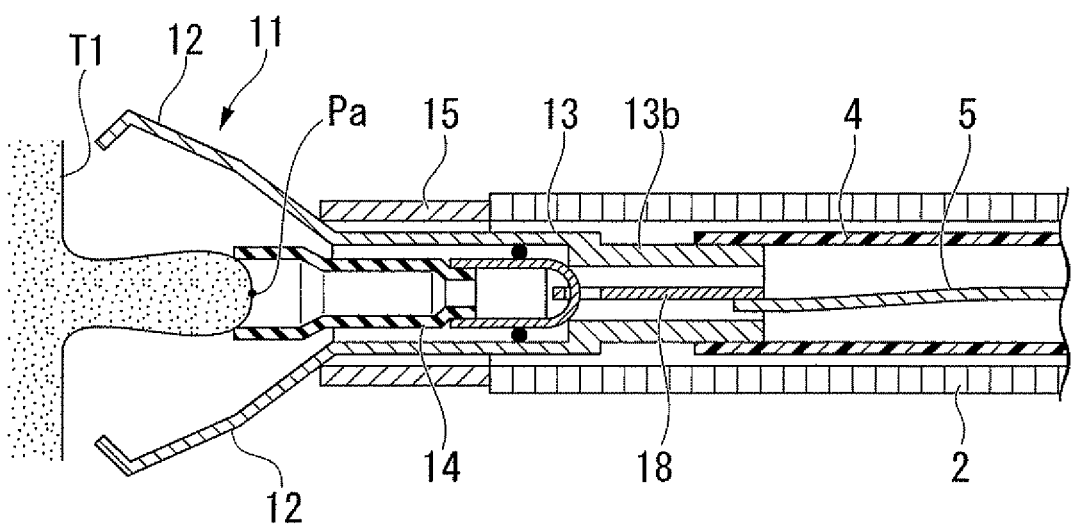
FIG. 7 is a cross-sectional view of essential parts explaining the operation of the grasper according to the modification of the first embodiment.
Figure 8:
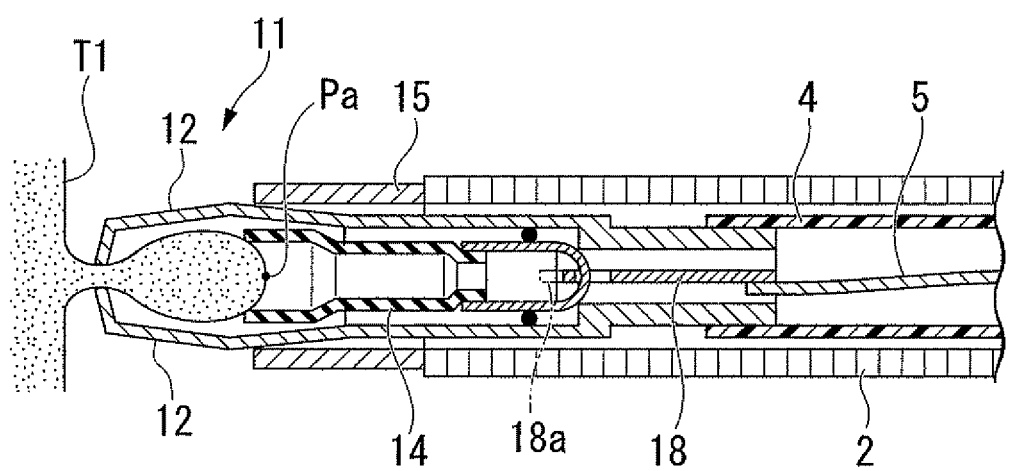
FIG. 8 is a cross-sectional view of essential parts explaining the operation of the grasper according to the modification of the first embodiment.

FIGS. 6 to 8 are diagrams showing a grasper and a clip according to a modification of the first embodiment of the invention. A difference between the modification and the first embodiment is as follows. In the first embodiment, as the slider 22 is pulled toward the proximal end, the operational wire 5 is moved toward the proximal end. In the modification, however, when a slider 30 is pulled toward the proximal end, the suction conduit 4 as well as the operational wire 5 are moved toward the proximal end.

The small-diameter portion 13b of the grasping pipe 13 is inserted into the distal end of the suction conduit 4 such that a gap does not occur between the large-diameter portion 13a and the distal end of the suction conduit 4. Further, the proximal end of the suction conduit 4 is inserted up to the middle position of the operator main body 20 so as to be fixed to the distal end portion of the slider 30 in an airtight state. The slider 30 has a cavity 31 formed therein, the cavity 31 communicating with a suction port 32. The suction port 32 is connected to a suction tube (not shown) though which a suction source such as a vacuum pump or the like is connected.

Now, the operation of the modification will be described. First, the distal end of the grasper A is inserted into the instrument channel of the endoscope which is inserted in advance into a natural opening of a patient. Then, the suction tube 14 positioned at the distal end of the grasper A is pressed against a bleeding point Pa of a body tissue T1. Then, the bleeding point Pa of the body tissue T1 is suctioned by the distal end of the suction tube 14. The above-described construction is the same as that of the first embodiment.

Thereafter, the slider 30 of the operator main body 20 is moved toward the proximal end, and the suction tube 14 is moved toward the proximal end through the operational wire 5 and the connection plate 18. Simultaneously, the suction conduit 4 is moved toward the proximal end. The suction tube 14 is moved inside the grasping pipe 13 such that the locked portion 17a at the proximal end side abuts against the distal end of the small-diameter portion 13b of the grasping pipe 13. Then, the suction tube 14 and the grasping pipe 13 are integrally moved toward the proximal end. As the grasping pipe 13 is moved toward the proximal end, the grasping arms 12 are closed by the pressing ring 15.

Subsequently, when the slider 30 is further moved toward the proximal end by a strong force, the locking portion 18a of the connection plate 18 is deformed so as to extend, as shown in FIG. 8. Then, the locking of the suction tube 14 to the locked portion 17a is released. The clip 11 of which the locking is released is indwelled in the body of the patient in a state where the body tissue T1 is grasped by the clip 11.

According to this modification, since a ligature point is accurately searched as in the first embodiment, the positioning of the clip 11 is easily performed. Further, since a portion which is being suctioned is clipped, it is possible to accurately ligature a portion, at which the body tissue T1 is positioned, during the clipping. In addition, when the clip 11 is detached from the locking portion 18a of the connection plate 18, the suction conduit 4 is moved in advance to the proximal end side. Thus, the joint length between the suction conduit 4 and the grasping pipe 13 (the length of an overlapped portion) can be reduced. As a result, the detaching operation of the clip 11 is easily performed.

FIGS. 9 to 20 are diagrams of modifications of the first embodiment, showing variations of a retracting portion which retracts a portion of a body tissue such that the portion is positioned between the grasping arms. The retracting portions shown in the modifications replace the suction tube 14 shown in FIG. 1. A construction in which the retracting portion is connected to the operational wire 5 through the locking portion 18a of the connection plate 18 is the same as that of the first embodiment.

Figure 9:
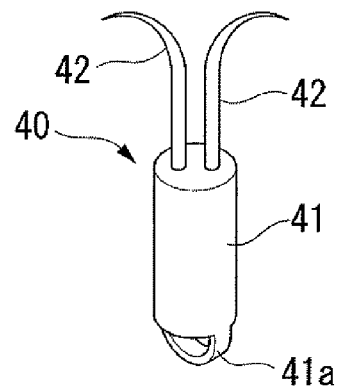
FIG. 9 is a perspective view of essential parts of a grasper according to another modification of the first embodiment of the invention.

The retracting portion 40 shown in FIG. 9 has a pair of curved needles 42 provided on the distal end of a cylindrical retracting base 41. The distal end portions of the curved needles 42 are curved in such a manner that the distal end portions expands outward and the sharp distal ends are directed to the proximal end side. The curved needles 42 are formed of a material which is not harmful to the body tissue and has elasticity. The retracting base 41 has a locked portion 41a formed at the proximal end side thereof the locked portion 41a being locked by the locking portion of the connection plate.

In this modification, since the air suction is not performed, the air suction system including the suction port 21, the suction conduit 4 and so on, which are provided in the slider 22 and the operator main body 20, do not need to be provided. This construction is also applied to modifications shown in FIGS. 10 to 17.

According to the retracting portion 40, the distal end of the retracting portion 40 projects further than those of the grasping arms. Therefore, when the retracting portion 40 is pressed against a predetermined place of a body tissue by an operation of the grasper or the operational wire, the curved needles 42 penetrate the body tissue such that the distal ends thereof are connected to a portion of the body tissue. After that, when the retracting portion 40 is pulled toward the proximal end by an operation of the operational wire, the body tissue connected to the distal ends of the curved needles 42 can be pulled toward the proximal end so as to be disposed between the grasping arms.

Such an operation is performed the same in the following modifications shown in FIGS. 10 to 12.

Figure 10:
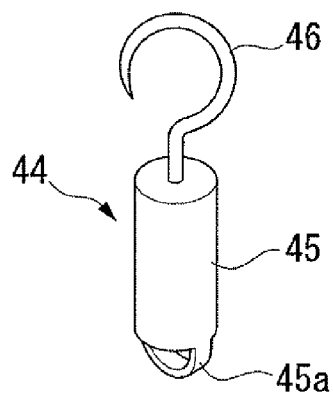
FIG. 10 is a perspective view of essential parts of a grasper according to another modification of the first embodiment of the invention.

A retracting portion 44 shown in FIG. 10 has a curved needle 46 provided at the distal end side of a cylindrical retracting base 45 and a locked portion 45a provided at the proximal end side of the retracting base 45. The curved needle 46 has a sharp distal end formed in substantially a Ω-shape.

Figure 11:
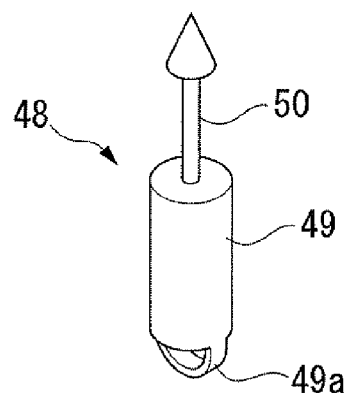
FIG. 11 is a perspective view of essential parts of a grasper according to another modification of the first embodiment of the invention.

A retracting portion 48 shown in FIG. 11 has a needle 50 provided at the distal end side of a cylindrical retracting base 49 and a locked portion 49a provided at the proximal end side of the retracting base 49. The needle 50 is formed in an arrow-head shape.

Figure 12:
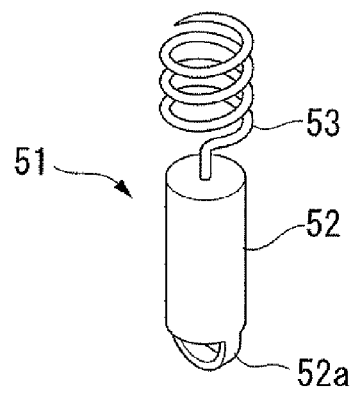
FIG. 12 is a perspective view of essential parts of a grasper according to another modification of the first embodiment of the invention.

A retracting portion 51 shown in FIG. 12 has a screw-shaped needle 53 provided at the distal end side of a cylindrical retracting base 52 and a locked portion 52a provided at the proximal end side of the retracting base 52. The screw-shaped needle 53 has a sharp distal end.

Figure 13A:
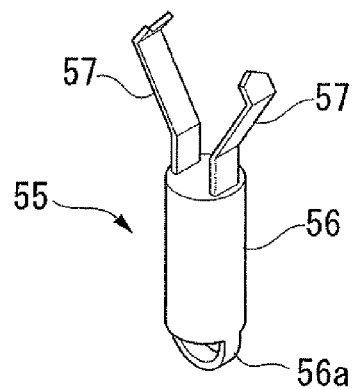
FIG. 13A is a perspective view of essential parts of a grasper according to another modification of the first embodiment of the invention.
Figure 13B:
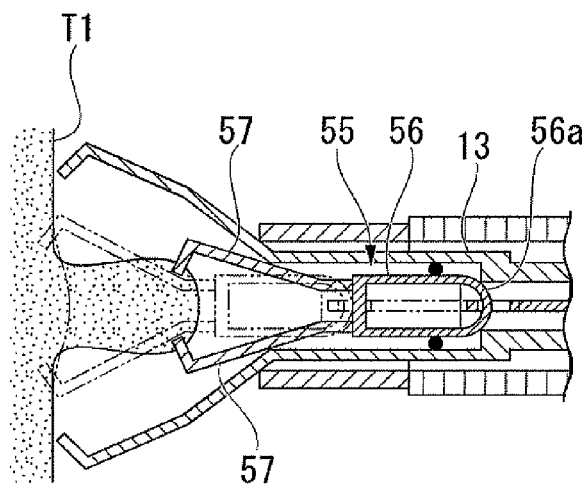
FIG. 13B is a cross-sectional view of essential parts of the grasper of FIG. 13A.

A retracting portion 55 shown in FIGS. 13A and 13B includes a pair of locking needles 57 provided at the distal end side of a cylindrical retracting base 56 and a locked portion 56a provided at the proximal end side of the retracting base 56. The pair of locking needles 57 have elasticity.

When the retracting portion 55 is pressed against a predetermined place of the body tissue by an operation of the operational wire or the like, the pair of locking needles 57 penetrate the body tissue such that the distal ends thereof lock a portion of the body tissue. After that, when the retracting portion 55 is pulled toward the proximal end by an operation of the operational wire, the locking needles 57 are inwardly pressed by the inner circumferential surface of the grasping pipe 13, as shown in FIG. 13B. Then, the body tissue can be clamped by the locking needles 57, which are closed, so as to be positioned between the grasping arms 12.

Figure 14:
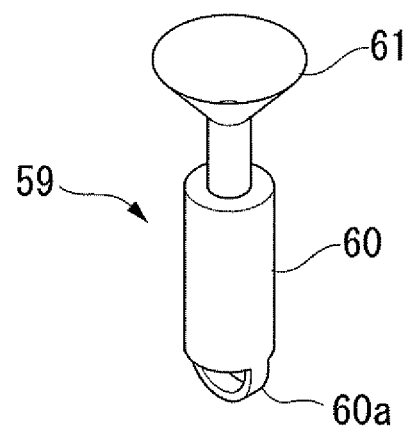
FIG. 14 is a perspective view of essential parts of a grasper according to another modification of the first embodiment of the invention.

A retracting portion 59 shown in FIG. 14 has a sucking disk 61 provided at the distal end side of a cylindrical retracting base 60 and a locked portion 60a provided at the proximal end side of the retracting base 60. The sucking disk 61 is formed of a flexible material such as rubber or the like.

Figure 15:
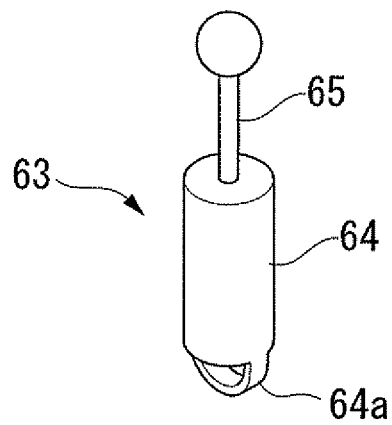
FIG. 15 is a perspective view of essential parts of a grasper according to another modification of the first embodiment of the invention.

A retracting portion 63 shown in FIG. 15 has an energy imparting portion 65 which passes through a cylindrical retracting base 64, the energy imparting portion 65 being formed of a conductive material. Further, the retracting portion 63 has a locked portion 64a provided at the proximal end side of the retracting base 64. The energy imparting portion 65 is connected to a high-frequency power supply through the operational wire such that a high-frequency current is supplied to the distal end of the energy imparting portion 65.

According to the retracting portion 63, the distal end of the energy imparting portion 65 is pressed against a predetermined portion of the body tissue by an operation of the operational wire or the like. In this state, a high-frequency current is supplied to the distal end of the energy imparting portion 65. At this time, the portion of the body tissue which is contacted with the energy imparting portion 65 is altered by high heat so as to be attached to the energy imparting portion 65. After that, when the retracting portion 63 is pulled toward the proximal end by an operation of the operational wire, the portion of the body tissue attached to the energy imparting portion 65 can be pulled toward the proximal end so as to be positioned between the grasping arms.

In the above-described modification, as a high-frequency current is supplied to the energy imparting portion 65, the portion of the body tissue is attached to the energy imparting portion 65. However, the present invention is not limited thereto; cold temperature may be supplied to the energy imparting portion 65 so as to momentarily freeze the body tissue. Then, a portion of the body tissue can be attached to the energy imparting portion 65. In this case, as for a supply unit of cold temperature, fro example, a supply unit using a Peltier element or a supply unit which supplies a cold refrigerant through a conduit line is considered.

Figure 16:
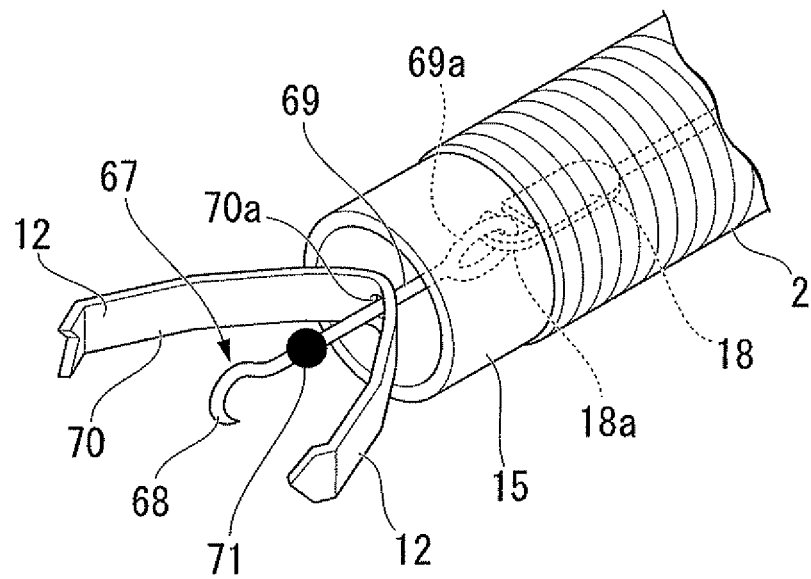
FIG. 16 is a perspective view of essential parts of a grasper according to another modification of the first embodiment of the invention.
Figure 17:
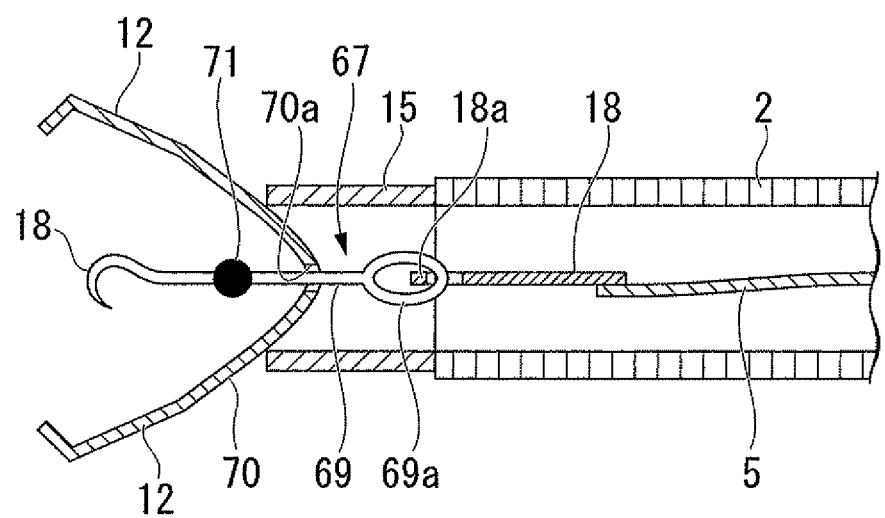
FIG. 17 is a cross-sectional view of essential parts of a grasper according to another modification of the first embodiment of the invention.

A retracting portion 67 shown in FIGS. 16 and 17 is composed of a rod member 69 having a hook portion 68 provided at the distal end thereof and a locked portion 69a provided at the proximal end thereof. The hook portion 68 serves to lock onto a body tissue, and the locked portion 69a is locked to the locked portion 18a of the connection plate 18. The rod member 69 passes through a through-hole 70a provided in the center of a bent plate 70 which is bent at a predetermined angle. The bent plate 70 is formed of an elastic material, and both end portions thereof serve as the grasping arms 12 which grasp a body tissue. The rod member 69 has a stopper piece 71 fixed to the middle portion of thereof the stopper piece 71 having a large diameter than the though-hole 70a.

According to the grasper of this modification, when the hook portion 68 provided at the distal end of the rod member 69 is pressed against a predetermined place of the body tissue by an operation of the operational wire, the hook portion 68 penetrates the body tissue so as to lock onto a portion of the body tissue. After that, when the rod member 69 is pulled toward the proximal end by an operation of the operational wire, the portion of the body tissue locked to the hook portion 68 is also pulled toward the proximal end so as to be disposed between the grasping arms 12.

When the rod member 69 is moved toward the proximal end, the stopper piece 71 abuts against the bent plate 70, and the central portion of the bent plate 70 is then retracted toward the proximal end integrally with the stopper piece 71. Accordingly, the grasping arms 12 are pressed inward by the pressing ring 15 so as to be closed. As a result, the portion of the body tissue can be grasped by the grasping arms 12.

After that, as the rod member 69 is retracted toward the proximal end by a stronger force, the locked portion 18a of the connection plate is deformed so as to extend, and the locking of the rod member 69 to the locked portion 69a is released, as in the above-described embodiment.

Instead of the construction in which the locking portion 18a of the connection plate is deformed so as to extend and the locking of the rod member 69 to the locked portion 69a is released, the following construction may be applied. That is, a fixing force of the stopper piece 71 to the rod member 69 is set in advance to be weak, with the rod member 69 and the operation wire being integrated. Further, the fixing of the stopper piece 71 to the rod member 69 is released to detach the rod member 69 from the clip 11 such that the clip 11 is indwelled in the body of the patient.

According to this modification, since the retracting portion is composed of only the rod member 69, the number of components can be reduced. Further, the grasping arms 12 can be constructed only by folding a band plate, and the grasping pipe is not required. Therefore, the grasping aims can be simply manufactured at a low cost. Such an effect is also obtained in the following modifications shown in FIGS. 18 to 20.

Figure 18:
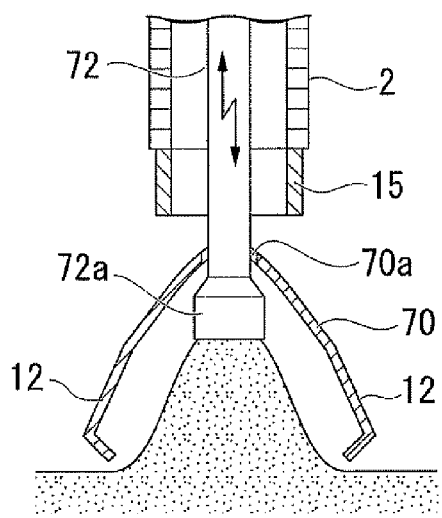
FIG. 18 is a perspective view of essential parts of a grasper according to another modification of the first embodiment of the invention.
Figure 19:
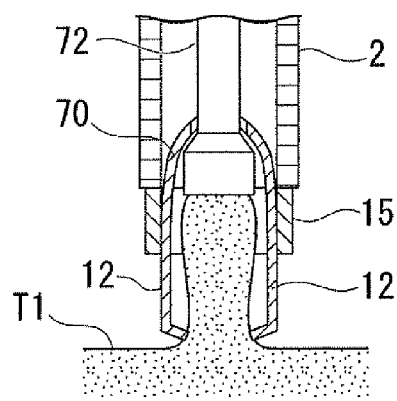
FIG. 19 is a perspective view explaining the operation of a grasper according to another modification of the first embodiment of the invention.
Figure 20:
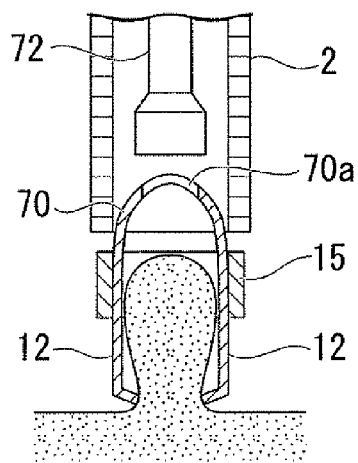
FIG. 20 is a perspective view explaining the operation of a grasper according to another modification of the first embodiment of the invention.

A retracting portion shown in FIGS. 18 to 20 are composed of a suction conduit 72 serving as a passage of air suction.

That is, the suction conduit 72 is inserted so as to advance and retract with respect to the coil sheath 2, the suction conduit 72 has a diameter-expanded portion 72a formed at the distal end thereof, and the diameter-expanded portion 72a has a larger diameter than the through-hole 70a of the bent plate 70. The proximal end of the suction conduit 72 is fixed to the slider of the operator main body.

According to the grasper of this modification, the operator main body is operated to press the diameter-expanded portion 72a of the suction conduit 72 against a predetermined portion of the body tissue T1 such that the portion is suctioned by the suction conduit 72. Then, the slider is moved toward the proximal end such that the suction conduit 72 is pulled toward the proximal end. Accordingly, the portion of the body tissue T1 suctioned and fixed to the diameter-expanded portion 72a of the suction conduit is also pulled toward the proximal end integrally with the suction conduit 72 so as to be disposed between the grasping arms 12 (refer to FIG. 18).

When the suction conduit 72 is moved toward the proximal end, the diameter-expanded portion 72a of the suction conduit abuts against the bent plate 70, and the central portion of the bent plate 70 is then retracted toward the proximal end integrally with the diameter-expanded portion 72a of the suction conduit. Accordingly, as shown in FIG. 19, the grasping arms 12 are inwardly pressed and closed by the pressing ring 15. As a result, the portion of the body tissue T1 is grasped by the grasping arms 12 (refer to FIG. 19).

After that, as the suction conduit 72 is retracted toward the proximal end through the slider by a stronger force, the diameter-expanded portion 72a of the suction conduit 72 is elastically deformed so as to contract, as shown in FIG. 20. Then, the diameter-expanded portion 72a of the suction conduit 72 slips out of the through-hole 70a of the bent plate 70. At this time, the diameter-expanded portion 72a may fracture or may be plastically deformed so as to slip out of the through-hole 70a of the bent plate 70. Accordingly, the clip 11 composed of the bent plate 70 and the pressing ring 15 is detached from the suction conduit 72 so as to be indwelled in the body of the patient, in a state where the grasping arms 12 are pressed by the pressing ring 15 so as to grasp the body tissue.

According to the first embodiment, before a portion of the body tissue is grasped by the plurality of grasping arms, the portion of the body tissue is retracted and positioned between the plurality of grasping arms by the retracting portion. Therefore, the portion which is to be grasped does not deviate, but can be accurately grasped. Further, even when a motion of the body tissue or the scope occurs, the body tissue is fixed by the retracting portion. Therefore, a deviation does not occur.

Further, by operating the operational elongate body composed of the operational wire or the suction conduit, it is possible to perform, for example, both the operation for retracting the suction portion toward the proximal end and the operation for closing the grasping arms.

[Second Embodiment]

Figure 21:
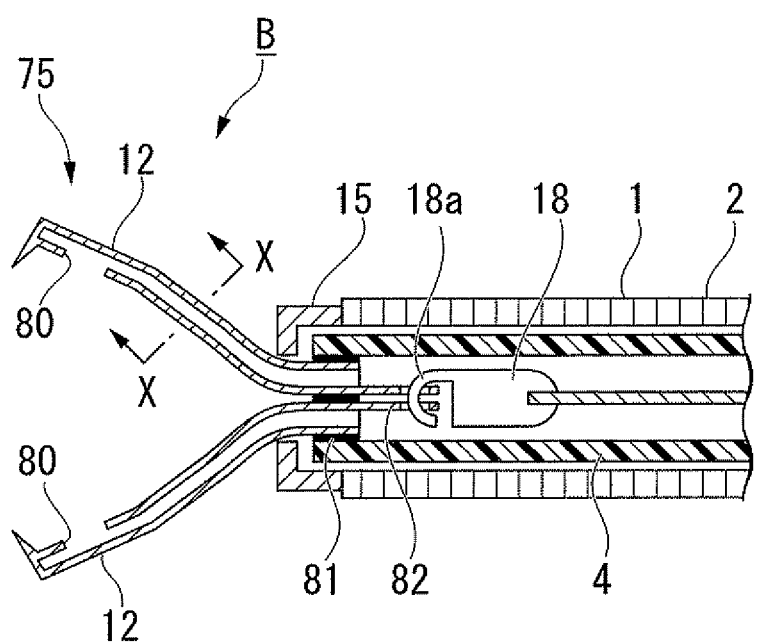
FIG. 21 is a cross-sectional view of essential parts of a grasper according to a second embodiment of the invention.
Figure 22:
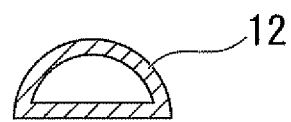
FIG. 22 is a cross-sectional view taken along X-X line of FIG. 21.

FIGS. 21 to 24 are diagrams showing a grasper and a clip according to a second embodiment of the invention. FIG. 21 is a cross-sectional view of the distal end portion of a grasper B, and FIG. 22 is a cross-sectional view taken along X-X line of FIG. 21.

As shown in FIG. 21, the clip 75 is detachably attached to the distal end of a coil sheath 2 of an introduction tube 1. The clip 75 has a pair of grasping arms 12 which grasp a body tissue and a pressing ring 15 which maintains the grasping arms 12 in a closed state. The grasping arms 12 have elasticity and are predisposed to spread out. As shown in FIG. 22, the grasping arms 12 have a hollow structure such that the distal end thereof is blocked. Further, the grasping arms 12 have a suction port 80 formed in the distal end portion of the inner wall thereof. The proximal ends of the grasping arms 12 are inserted into a suction conduit 4 in an airtight state so as to slide through a seal member 81. The grasping arms 12 have a locked portion 82 provided at the proximal end side, the locked portion 82 being locked to the locking portion 18a of the connection plate 18. The space within the grasping arms 12 is connected to an air suction source such as a vacuum pump through the suction conduit 4.

According to the grasper B of the second embodiment, the introduction tube 1 is inserted into an instrument channel of an endoscope, and the locking of the introduction tube 1 by an outer tube (not shown) is released in the vicinity of a ligature point so as to open the pair of grasping arms 12.

Figure 23:
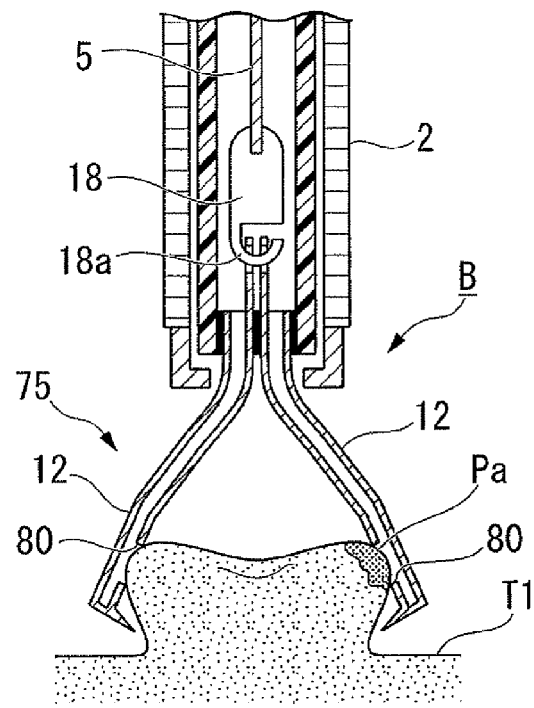
FIG. 23 is a perspective view explaining the operation of the grasper according to the second embodiment of the invention.

As shown in FIG. 23, the suction ports 80 of the grasping arms 12 is put toward a bleeding point Pa or the vicinity of the bleeding point Pa so as to suck the bleeding point Pa through conduit lines within the grasping arms 12. Then, a body tissue T1 including the bleeding point Pa is pulled between the grasping arms 12. Bleeding from the bleeding point Pa is temporarily arrested by the suction. The pulled body tissue T1 is checked through an observation device of the endoscope. When the bleeding point Pa deviates, the position of the grasping arms 12 is returned to a predetermined point by displacement while the suction is continued.

Figure 24:
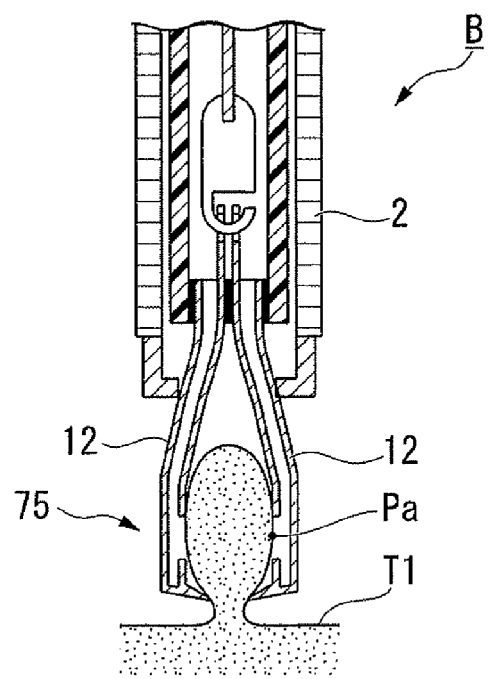
FIG. 24 is a perspective view explaining the operation of the grasper according to the second embodiment of the invention.

When the grasping arms 12 are moved to the proper position, the slider of the operator main body (not shown) is operated to close the grasping arms 12. Since the grasping arms 12 are closed while the body tissue is suctioned by the suction ports 80, the body tissue T1 is clipped as shown in FIG. 24.

In the clip 75, the position at which the bleeding is temporarily arrested can be set to an actual ligature point. The other effects are the same as those of the first embodiment.

In the clip 75, the suction port 80 may be formed in only one of the grasping arms 12 such that while a body tissue is suctioned by the suction port 80, the body tissue may be grasped by the grasping arms 12.

In this embodiment shown in the drawings, the suction port 80 is formed in a position in the proximal side to an operator from the distal end of the inner wall of the grasping claw 12. However; the position of the suction port 80 is not limited thereto. That is, the suction portion 80 may be formed at the distal end of the inner wall or at the distal end of the outer wall of the grasping claw 12. As long as the suction port 80 may be formed in a position at which a body tissue can be suctioned when the suction port 80 is opposed to the body tissue, the position is allowed.

According to the second embodiment, a position at which bleeding is temporarily arrested can be set to an actual ligature point, in addition to the effects exhibited by the first embodiment. Further, since the grasping arms have a hollow structure, the function of the grasping arms which grasp a body tissue and the function of the retracting portion which retracts a body tissue between the grasping arms can be combined. Therefore, it is possible to reduce the number of components.

[Third Embodiment]

FIGS. 25 to 32 are diagrams showing a grasper and a clip according to a third embodiment of the invention. FIG. 25A is a cross-sectional view of the distal end portion of a grasper C, and FIG. 25B is a perspective view of the distal end portion of the grasper C.

Figure 25A:
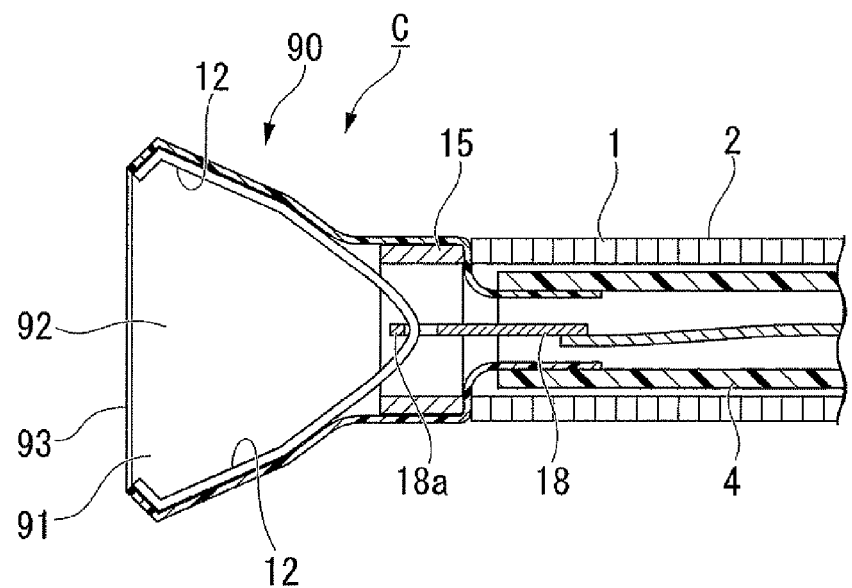
FIG. 25A is a cross-sectional view of essential parts of a grasper according to a third embodiment of the invention.
Figure 25B:
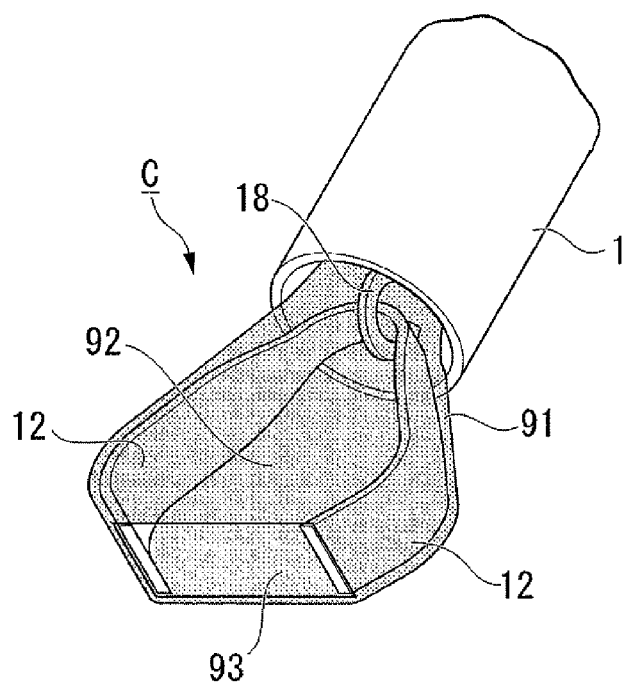
FIG. 25B is a perspective view of essential parts of the grasper according to the third embodiment of the invention.
Figure 26A:
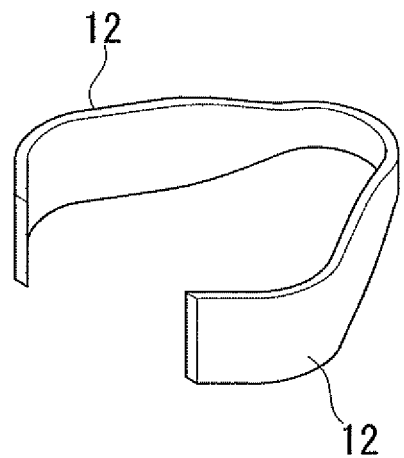
FIGS. 26A and 26B are perspective views of grasping arms of the grasper according to the third embodiment of the invention.
Figure 26B:
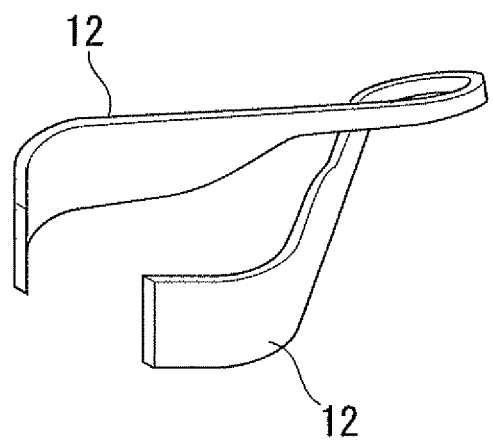

As shown in FIGS. 25A and 25B, the clip 90 is detachably attached to the distal end of an introduction tube 1 having a coil sheath 2 and an outer tube (not shown) disposed outside the coil sheath 2. The clip 90 has a pair of grasping arms 12 which grasp a body tissue and a pressing ring 15 which maintains the grasping arms 12 in a closed state. The grasping arms 12 have elasticity and are predisposed to spread out. The grasping arms 12 are formed by folding the middle portion of a band-shaped member such that the grasping arms 12 are formed in the both end portions of the band-shaped member. The central folded portion serves as a locked portion 12a which is locked to a locking portion 18a of a connection plate 18. As shown in FIG. 26A, the grasping arms 12 may be formed by simply folding the middle portion of a band-shaped member at a predetermined angle. Alternatively, as shown in FIG. 26B, the grasping arms 12 may be formed by twisting a band-shaped member a plurality of times.

A film 91 is bonded around the grasping arms 12 such that the grasping arms 12 are surrounded by the film 91. The film 91 is inserted into the distal end of a suction conduit 4. The film 91 may be bonded to the grasping arms 12 through an adhesive or the like, and may be bonded to the distal end portion of the suction conduit 4. Further, the film 91 is formed of a material that does not obstruct visibility. A space 92 is defined by the pair of grasping arms 12 the film 91, the pressing ring 15, and the distal end portion of the suction conduit 4, and an opening 93 is formed by the grasping arms 12 and the film 91. The space 92 defined by the film 91 and so on is connected to an air suction source (not shown) through the suction conduit 4.

Figure 27:
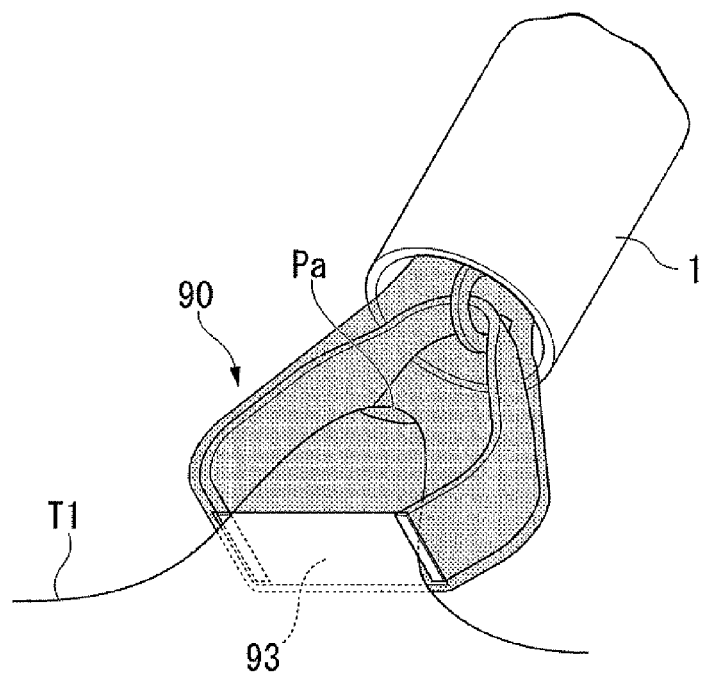
FIG. 27 is a perspective view explaining the operation of the grasper according to the third embodiment.

When a body tissue is ligatured by the clip 90, the introduction tube 1 is inserted into an instrument channel of an endoscope, and the pair of grasping arms 12 are opened in the vicinity of a ligature point. Accordingly, the film 91 is spread. In this case, the film 91 may be constructed so as to protect the grasping arms 12 such that damage is not applied to the instrument channel. As shown in FIG. 27, the opening 93 is combined with a bleeding point Pa such that suction by the air suction source through the suction conduit 4 begins. Then, a body tissue T1 including the bleeding point Pa is suctioned into the clip 90 from the opening 93 such that bleeding is temporarily arrested. The suctioned body tissue T1 is checked through an observation device of the endoscope. When the bleeding point Pa deviates, the position of the grasping arms 12 is displaced to a proper point while the suction is continued.

Figure 28:
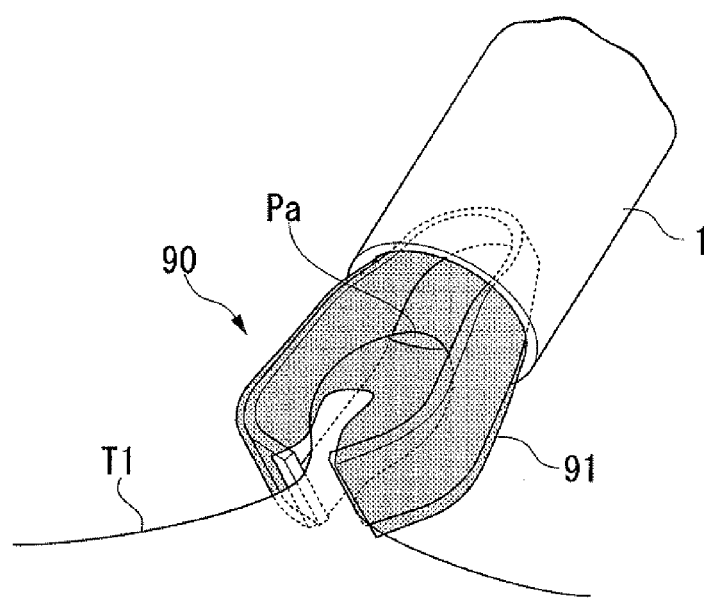
FIG. 28 is a perspective view explaining the operation of the grasper according to the third embodiment.

When a proper position is suctioned into the clip 90, the slider of the operator main body is operated to close the pair of grasping arms 12. The position of the opening 93 serving as a suction port substantially coincides with the distal end of the grasping arms 12. Therefore, as shown in FIG. 28, when the body tissue T1 is suctioned into the clip 90 from the opening 93, the bleeding point Pa is positioned between the pair of grasping arms 12. In this state, as the pair of grasping arms 12 are closed, the tissue in the vicinity of the bleeding point Pa of the body tissue T1 can be reliably clipped.

In the clip 90, a wider portion including a position at which bleeding is temporarily arrested can be clipped as an actual ligature point. Further, since the suction port is large, a body tissue can be retracted by a stronger force. The other effects are the same as those of the first embodiment.

FIGS. 29 to 32 are diagrams showing modifications of the third embodiment.

Figure 29:
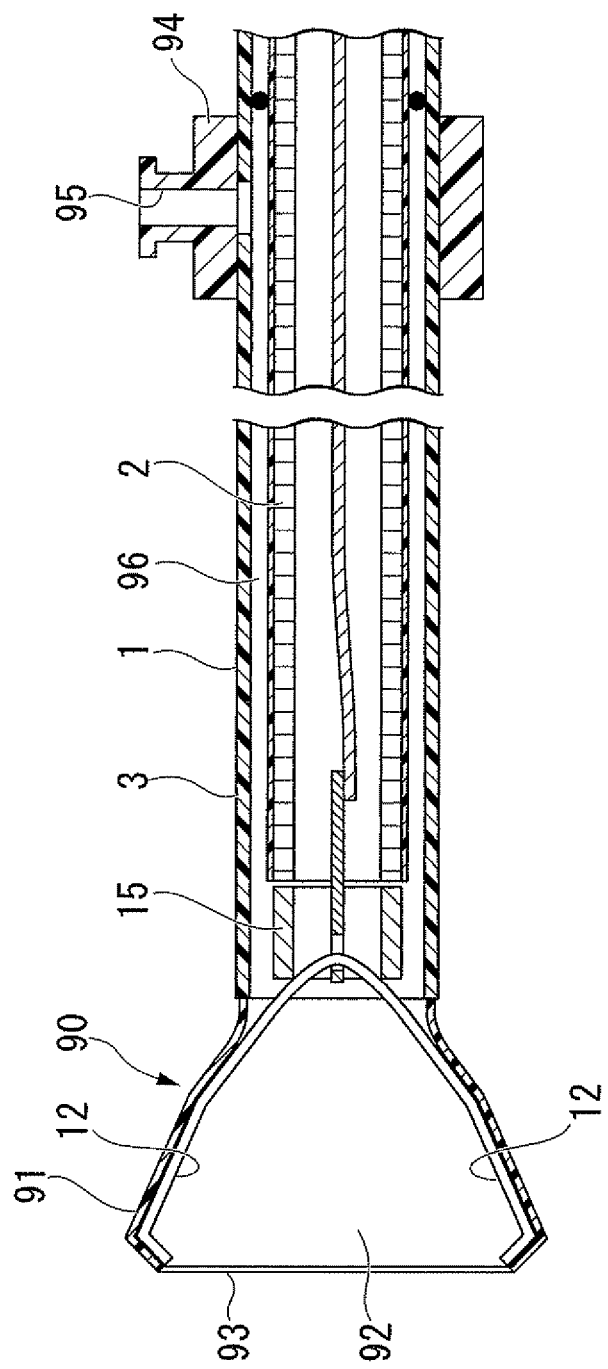
FIG. 29 is a cross-sectional view of a grasper according to a modification of the third embodiment of the invention.

In a modification shown in FIG. 29, the proximal end side of the film 91 is fixed to the distal end of the outer tube 3 of the introduction tube 1, not the suction conduit 4, by a proper fixing method such as adhesion or thermal adhesion. In this case, a suction joint 94 is attached to the outer circumference of the introduction tube 1, and an air suction source such as a vacuum pump or the like is connected to a suction port 95 of the suction joint 94. That is, an air passage for sucking the air from the space 92 defined by the pair of grasping arms 12, the film 91, and the pressing ring 15 is secured by a space 96 defined between the outer tube 3 and the coil sheath 2 of which the outer surface is coated.

Further, when a body tissue is suctioned from the opening 93, a bleeding point is positioned between the pair of grasping arms 12. In this state, as the pair of grasping arms 12 are closed; the tissue in the vicinity of the bleeding point of the body tissue can be reliably clipped.

Figure 30:
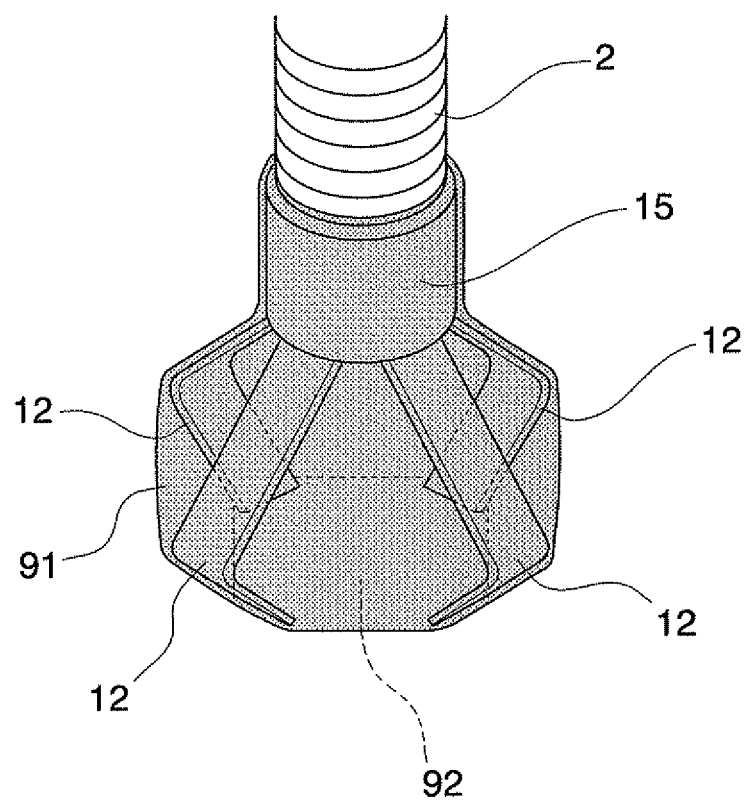
FIG. 30 is a perspective view of a grasper according to another modification of the third embodiment of the invention.
Figure 31:
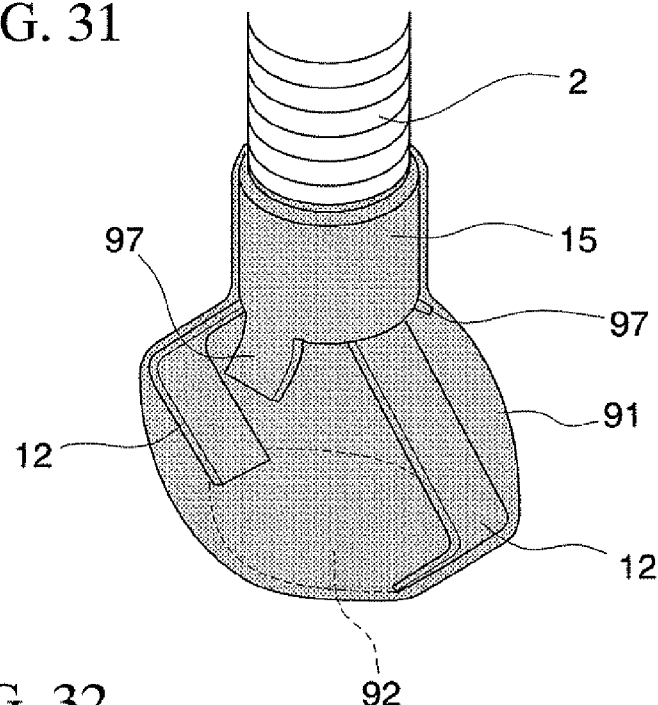
FIG. 31 is a perspective view of a grasper according to another modification of the third embodiment of the invention.

In a modification shown in FIG. 30, four grasping arms, not two grasping arms, are provided. In a modification shown in FIG. 31, a projection 97 which is curved outward is formed on either side between the pair of grasping arms 12.

In these modifications, when the air is suctioned, the film 91 is inwardly concaved. Therefore, it can be prevented that the space 92 is not secured within the film 91 in advance. That is, more than three of the grasping arms 12 and the projections 97 support the film 91 from the inside, which makes it possible to prevent the film 91 from being deformed.

Figure 32:
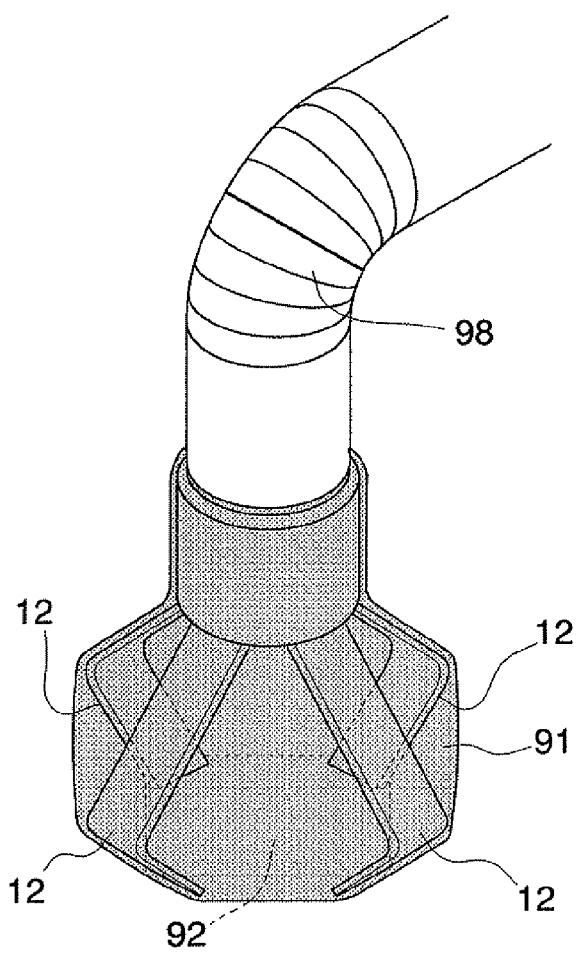
FIG. 32 is a perspective view of a grasper according to another modification of the third embodiment of the invention.

In a modification shown in FIG. 32, a flexible portion 98 is provided in the middle portion of the introduction tube 1. Accordingly, even when the introduction tube 1 is disposed obliquely with respect to a body tissue, the opening 93 of the space 92 surrounded by the film 91 can be opposed to the body tissue by bending the flexible portion 98 of the introduction tube 1 at a proper angle.

In the above-described modifications, one film is bonded around the grasping arms 12. Without being limited thereto, however, the film 91 may be divided into a plurality of films. Then, the side end portions of the divided films may be bonded to the grasping claw 12 such that the space 92 for air suction is formed between the films.

According to the third embodiment, a wider portion can be clipped as an actual ligature point than in the first and second embodiment, in addition to the effects exhibited by the first embodiment. Further, since the suction port is large, a body tissue can be retracted by a stronger force. Further, the retracting portion which retracts a body tissue between the grasping arms is constructed by providing the film around the grasping arms or between the grasping arms. Therefore, the number of components can be reduced.

[Fourth Embodiment]

Figure 33:
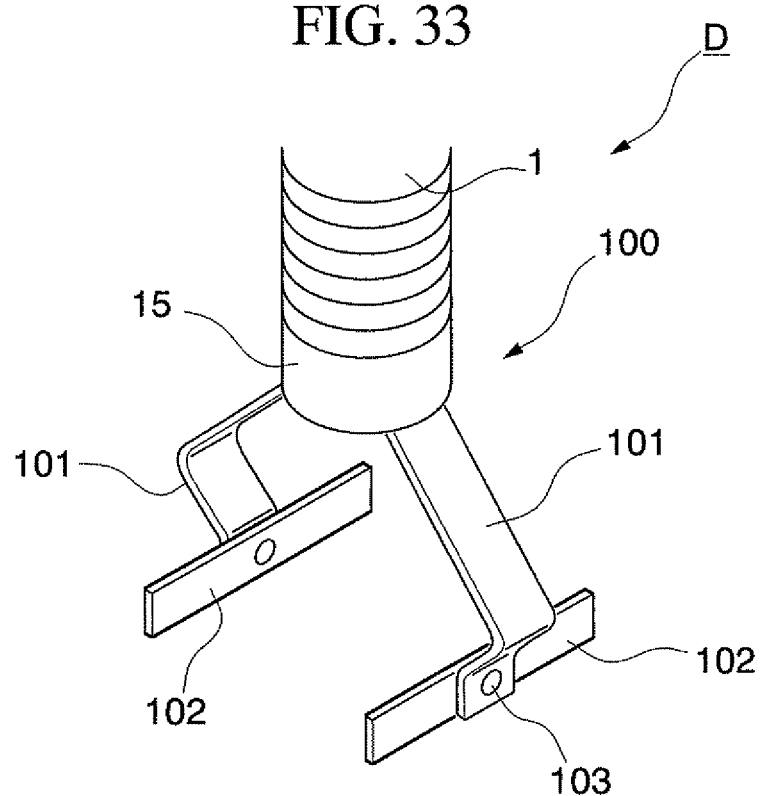
FIG. 33 is a perspective view of a grasper according to a fourth embodiment of the invention.

FIGS. 33 to 37 are diagrams showing a grasper and a clip according to a fourth embodiment of the invention. FIG. 33 is a perspective view of the distal end portion of a grasper D.

In the fourth embodiment, the following problems can be solved.

In a conventional clip, the distal end of grasping arms is so thin that the positioning with respect to a ligature point needs to be performed in a delicate manner. Further, even after the positioning is performed, the clip needs to be moved when clipping is performed. Further, as the grasping arms are vertically erected so as to be pressed against a body tissue, the body tissue is retracted into surfaces formed between the grasping arms. Therefore, although the clipping can be performed best, there are difficulties in adjusting the direction of the clipping if the procedure is performed via entry through the mouth.

As shown in FIG. 33, the clip 100 has a pair of grasping arms 101 which grasp a body tissue and a pressing ring 15 which maintains the pair of grasping arms 101 in a closed state. The grasping arms 101 have proper elasticity and are predisposed to spread out. Each of the grasping arms 101 has a rotating arm 102 formed at the distal end thereof, the rotating arm 102 being rotatably attached by a rotating mechanism composed of a pin 103.

The grasping arms 101 are formed by folding the middle portion of a band-shape member such that the distal ends thereof are opened. The length of the rotating arm 102 is larger than the width of the grasping arm 101, and the central portion of the rotating arm 102 is fastened to the pin 103. The rotation center of the rotating arm 102 is set to an attachment position, and the attachment position corresponds to the center of the rotating arm 102 in the longitudinal direction thereof, as shown in FIG. 33. Without being limited thereto, however, the attachment position may be set to the longitudinal distal end of the rotating arm 102.

Figure 34:
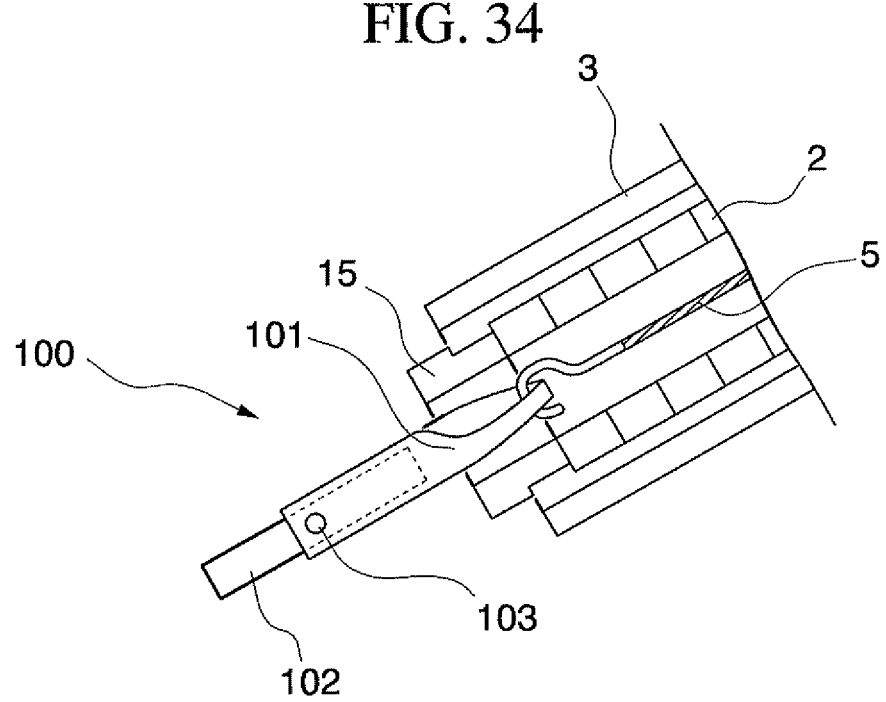
FIG. 34 is a cross-sectional view explaining the operation of the grasper according to the fourth embodiment of the invention.

As shown in FIG. 34, when the rotating arm 102 is rotated around the pin 103 so as to be disposed substantially in parallel to the grasping arm 101, the entire clip 100 can be retracted into the outer tube 3. At this time, the pair of grasping arms 101 are pressed by the outer tube 3 so as to be closed.

Figure 35:
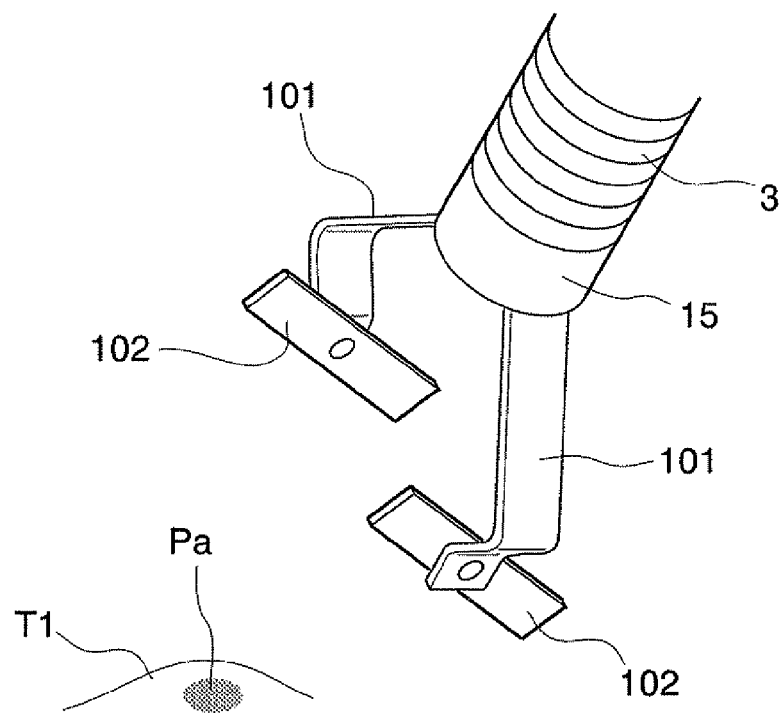
FIG. 35 is a perspective view explaining the operation of the grasper according to the fourth embodiment of the invention.
Figure 36:
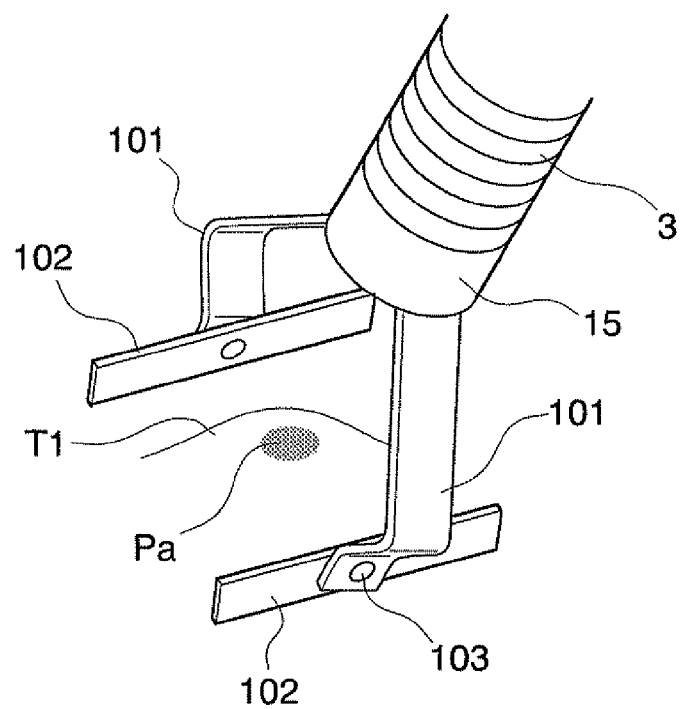
FIG. 36 is a perspective view explaining the operation of the grasper according to the fourth embodiment of the invention.
Figure 37:
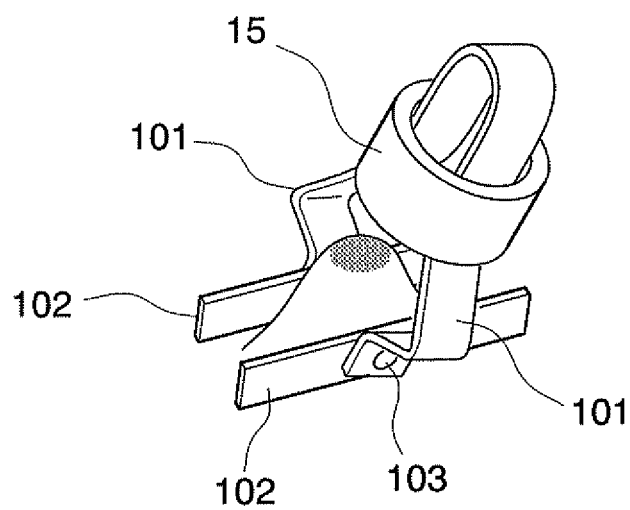
FIG. 37 is a perspective view explaining the operation of the grasper according to the fourth embodiment of the invention.

When a body tissue is to be clipped, the outer tube 3 housing the clip 100 is inserted into an instrument channel of an endoscope, and the clip 100 is pushed out in the tissue in the vicinity of a ligature point. As shown in FIG. 35, the grasping arms 101 open due to their restoring force, and the rotating arms 102 rotate around the pins 103 so that the clip 100 has a substantially T shape, when seen from the side.

When the rotating arms 102 are pressed against a body tissue T1 which is to be clipped, the rotating arms 102 are rotated so as to be substantially parallel to the body tissue T1 (refer to FIG. 36), even though the rotating arms 102 approach the body tissue T1 such that the longitudinal direction of the grasping arms 101 is oblique with respect to the body tissue T1, as shown in FIG. 35. Then, when the grasping arms 101 are retracted into the pressing ring 15 by operating the slider of the operator main body, the grasping arms 101 are closed in such a manner that the body tissue T1 is interposed between the rotating arms 102. The rotating arms 102 are disposed in substantially parallel to the body tissue T1, and surfaces formed by the rotating arms 102 of the clip 100 are parallel to the body tissue. Therefore, a force is evenly applied to the entire rotating arms 102 to clip the body tissue T1.

When the slider is pulled by a stronger force, the locking portion of the connection plate is plastically deformed to extend, and the connection to the grasping arms 101 is released. The clip 100 of which the connection is released is indwelled in the body of a patient in a state where the body tissue T1 is grasped (refer to FIG. 37).

In this clip 100, since the rotating arms 102 are abutted on the tissue in the longitudinal direction thereof a quantity of tissue which is gasped at one time can be increased. Further, even when the position of the rotating arms 102 slightly deviates, the body tissue T1 can be reliably clipped. Therefore, the positioning is easily performed, and delicate adjustment is not necessary.

As the rotating arm 102 is rotated around the pin 103, the rotating arm 102 can be disposed in parallel to a tissue at all times. Therefore, the clipping is optimally performed regardless of the approach direction of the clip 31.

Further, as the rotating arm 102 is rotated around the pin 103 such that the clip 100 has a substantially I shape, when seen from the side, the clip 100 can be housed in the outer tube 3 and can be inserted into the thin instrument channel.

According to the fourth embodiment of the invention, since the rotating arms 102 are abutted on the tissue in the longitudinal direction thereof, a quantity of tissue which is grasped at one time can be increased. Further, although the position of the rotating arms 102 slightly deviates, the body tissue T1 can be reliably clipped. Therefore, the positioning is easily performed, and delicate adjustment is not necessary. Further, the clipping is optimally performed regardless of the approach direction of the grasping tool.

[Fifth Embodiment]

Figure 38:
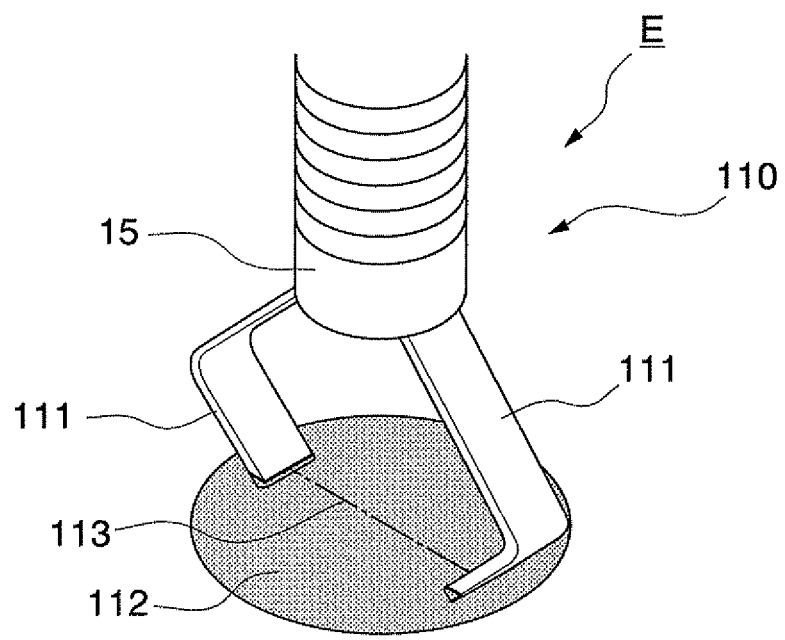
FIG. 38 is a perspective view of a grasper according to a fifth embodiment of the invention.

FIGS. 38 to 42 are diagrams showing a grasper and a clip according to a fifth embodiment of the invention. FIG. 38 is a perspective view of the distal end portion of a grasper E.

In this embodiment, the following problems are to be solved.

When bleeding occurs during clipping, it is difficult to check the bleeding point. When the surrounding of a bleeding point is contaminated with blood or mucus, it is also difficult to check the bleeding point. Further, it is difficult to predict a position when the clip is closed. In order to make a clip reliably bite into a tissue, the clip needs to be sufficiently pressed against the tissue. However, the operation of pressing the clip against the tissue is performed in a direction away from an endoscope. Therefore, visibility decreases.

As shown in FIG. 38, the clip 110 has a pair of grasping arms 111, 111 which grasp a body tissue and a pressing ring 15 which is disposed at the distal end of the introduction tube 1 and maintains the pair of grasping arms 111 in a closed state. The grasping arms 111 have proper elasticity and are predisposed to spread out The grasping arms 111 have a film 112 attached to the distal ends thereof. The film 112 is formed in a circle having a diameter which is larger than the distance between the grasping arms 111 when they widen. The film 112 is disposed substantially in a direction crossing the longitudinal direction of the clip 110 and is formed of a transparent material with flexibility. The film 112 has a ligature line 113 provided thereon, the ligature line 113 indicating a trajectory along which the distal ends of the grasping arms 111 move when the grasping arms 111 are closed. The film 112 may be formed of an opaque material, and the ligature line 113 may not be provided.

Figure 39:
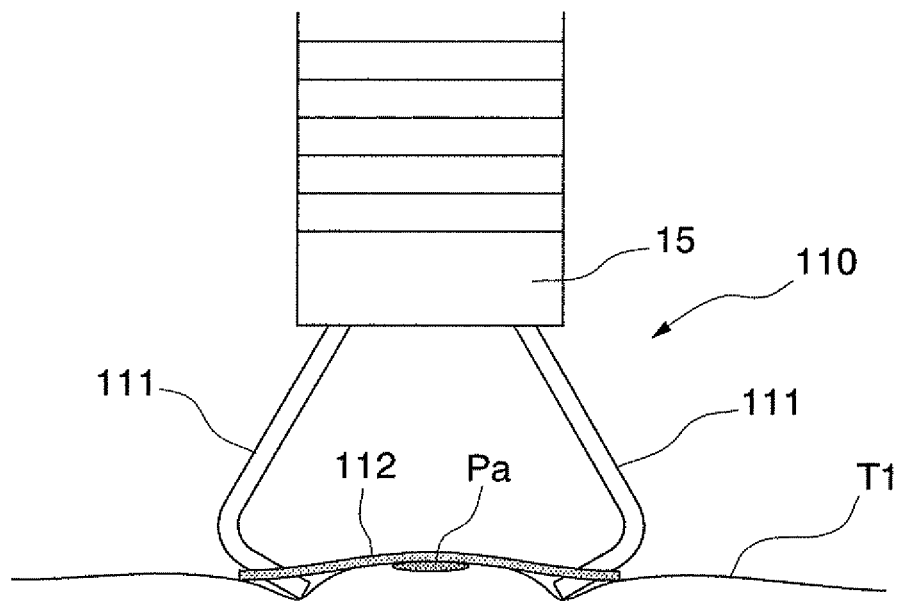
FIG. 39 is a cross-sectional view explaining the operation of the grasper according to the fifth embodiment of the invention.
Figure 40:
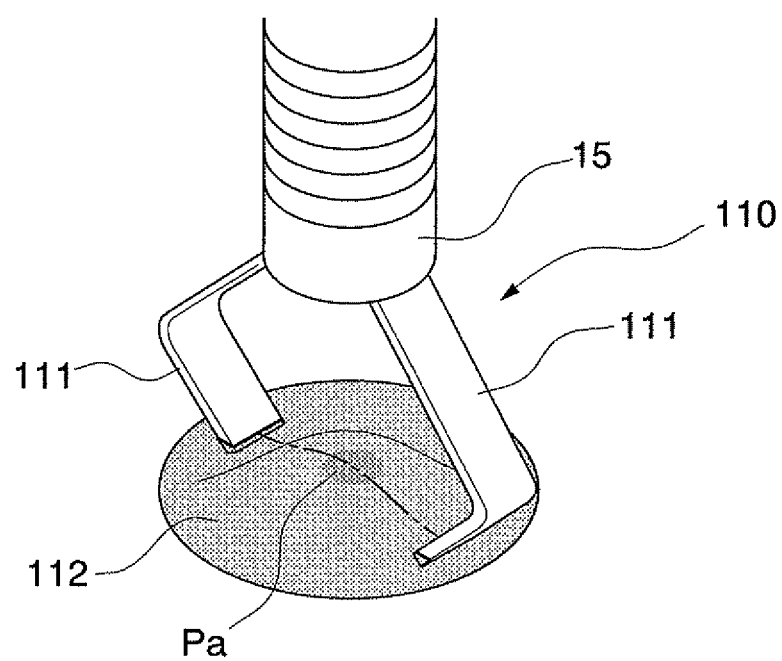
FIG. 40 is a perspective view explaining the operation of the grasper according to the fifth embodiment of the invention.

When a tissue is grasped by the clip 110, the introduction tube 1 is inserted into an instrument channel of an endoscope inserted into a natural opening, and the pair of grasping arms 111 are opened. As shown in FIGS. 39 and 40 the film 112 is pressed against a bleeding point Pa. As the film 112 is pressed against the bleeding point Pa, pressure is applied to the bleeding point Pa to stop bleeding. The bleeding point Pa can be easily checked through the transparent film 112. Therefore, when a positional deviation occurs, the clip 110 is moved. At this time, in the film 1/2 on which the ligature line 113 is provided, when the clip 110 is disposed in such a manner that the bleeding point Pa is positioned on the ligature line 113, the bleeding point Pa can be reliably grasped during the clipping. Accordingly, the bleeding can be arrested.

When the clip 110 is disposed in a proper position, the pair of grasping arms 111 are closed by operation at the proximal side of the endoscope, for example, by a slider or the like. Then, the tissue T1 is clipped by the clip 110 such that the portion at which the bleeding is temporarily arrested is centered.

In this clip 110, since the bleeding point is pressured by the film 112, the bleeding can be temporarily slowed. Further, since the film 112 is formed of a transparent material, the bleeding point Pa is easily checked when the film 112 is pressed against the tissue.

Since the ligature line 113 is provided on the film 112, it is possible to check in advance a portion which is to be grasped when the clip 110 is closed.

Figure 41:
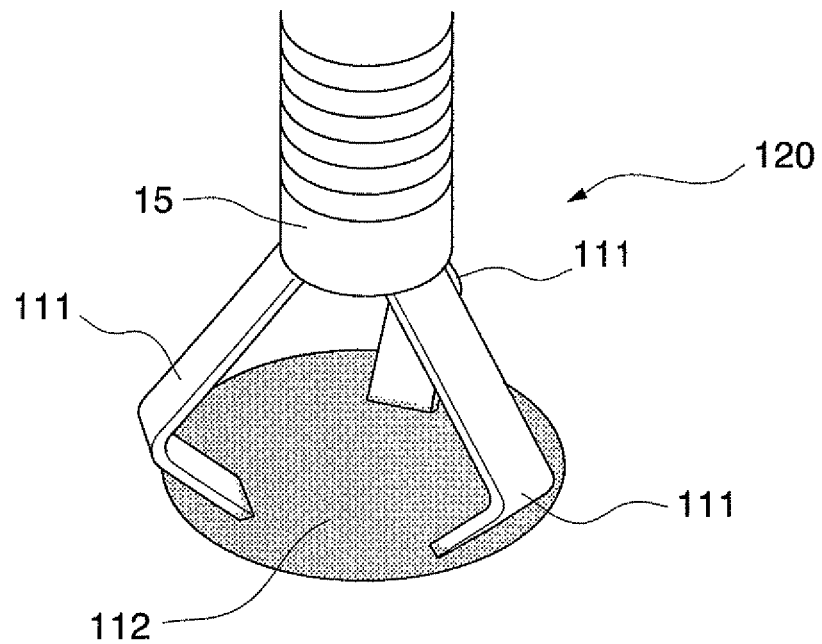
FIG. 41 is a perspective view of a grasper according to a modification of the fifth embodiment of the invention.
Figure 42:
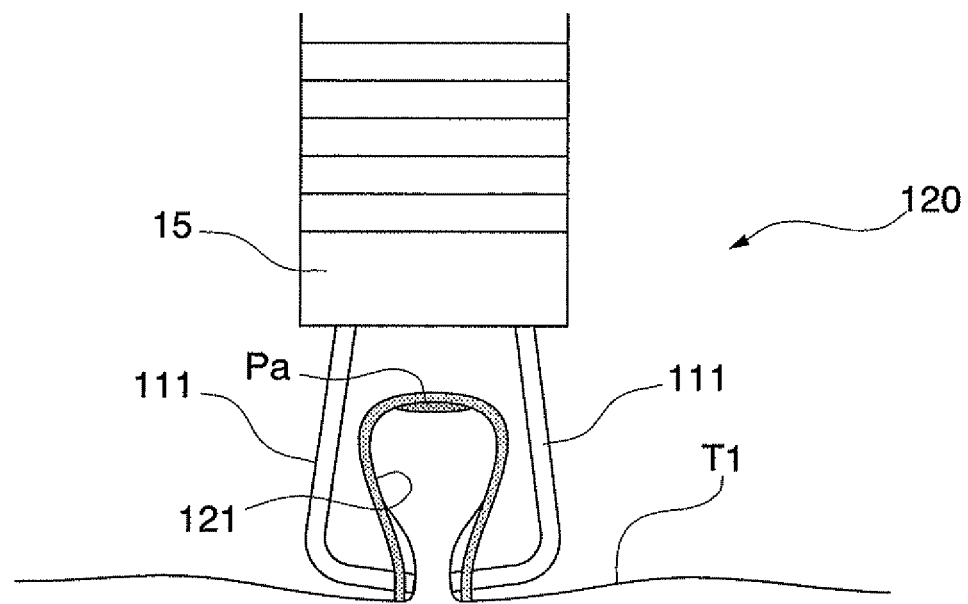
FIG. 42 is a perspective view of a grasper according to another modification of the fifth embodiment of the invention.

FIGS. 41 and 42 are diagrams showing modifications of the fourth embodiment.

In a modification shown in FIG. 41, a clip 120 has three grasping arms 111. In a modification shown in FIG. 42, an adhesive film is used as the film 121. As shown in FIG. 42, the body tissue T1 stuck on the film 121 is naturally lifted during the clipping. Therefore, although the grasping arms 111 are not strongly pressed against the tissue T1, the clipping can be sufficiently performed.

According to the fifth embodiment of the invention, even when the surrounding of a bleeding point is contaminated with blood and mucus during the clipping, the bleeding point can be checked, and it is easy to predict a position when the clip is closed. Further, even when the clip is pressed against the tissue, it is possible to secure excellent visibility.

[Sixth Embodiment]

Figure 43:
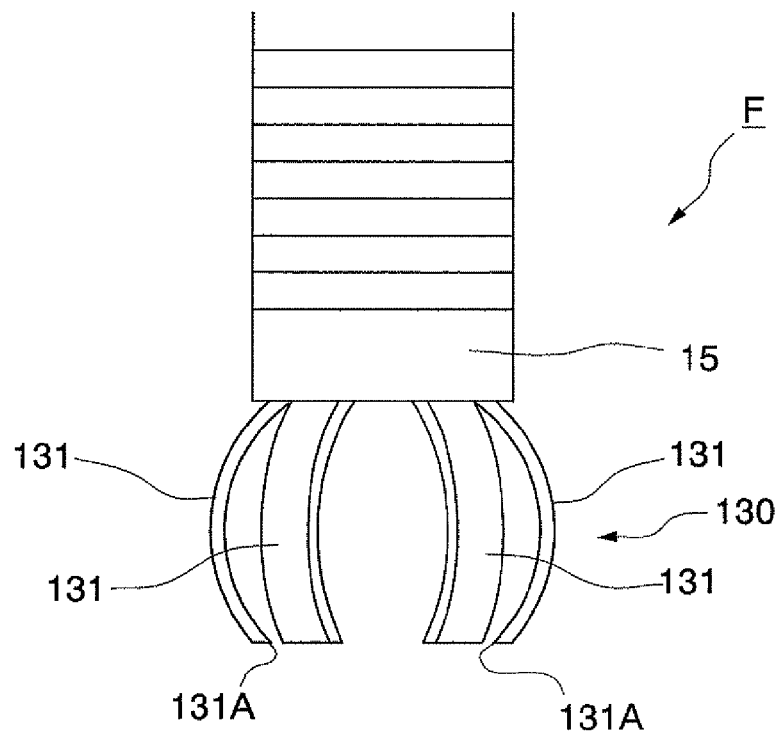
FIG. 43 is a perspective view of a grasper according to a sixth embodiment of the invention.

FIGS. 43 to 46 are diagrams showing a grasper and a clip according to a sixth embodiment of the invention. FIG. 43 is a perspective view of the distal end portion of a grasper F.

As shown in FIG. 43, a clip 130 has a plurality of grasping arms 131 extending from the introduction tube 1. The respective grasping arms 131 are curved in such a manner that the central portions thereof swell to be larger than the diameter of the introduction tube 1 after being pushed out of the introduction tube 1 and the distal end portions 131A thereof come close to one another. Each of the grasping arms 131 is formed in an arch shape as a whole.

Figure 44:
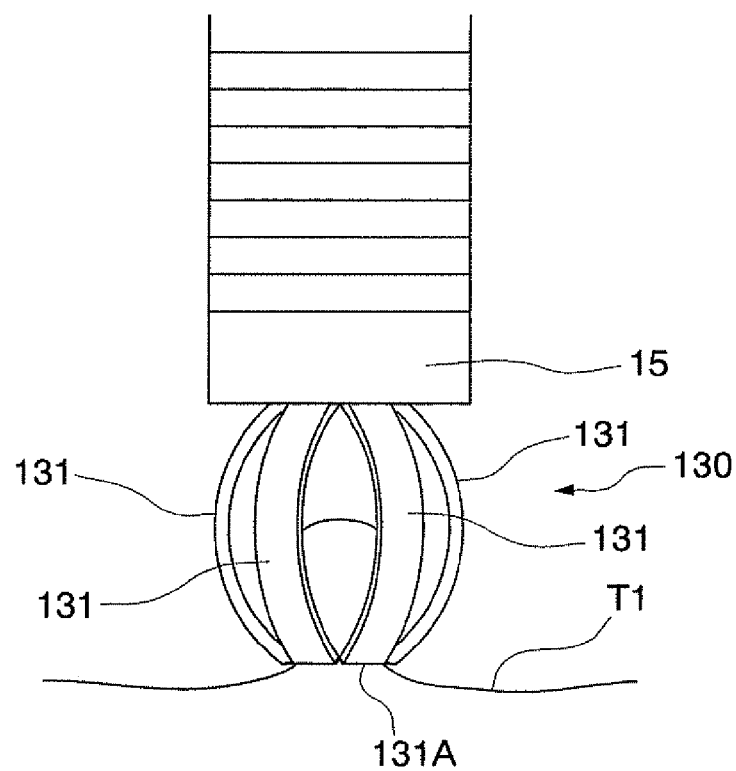
FIG. 44 is a perspective view explaining the operation of the grasper according to the sixth embodiment of the invention.
Figure 45:
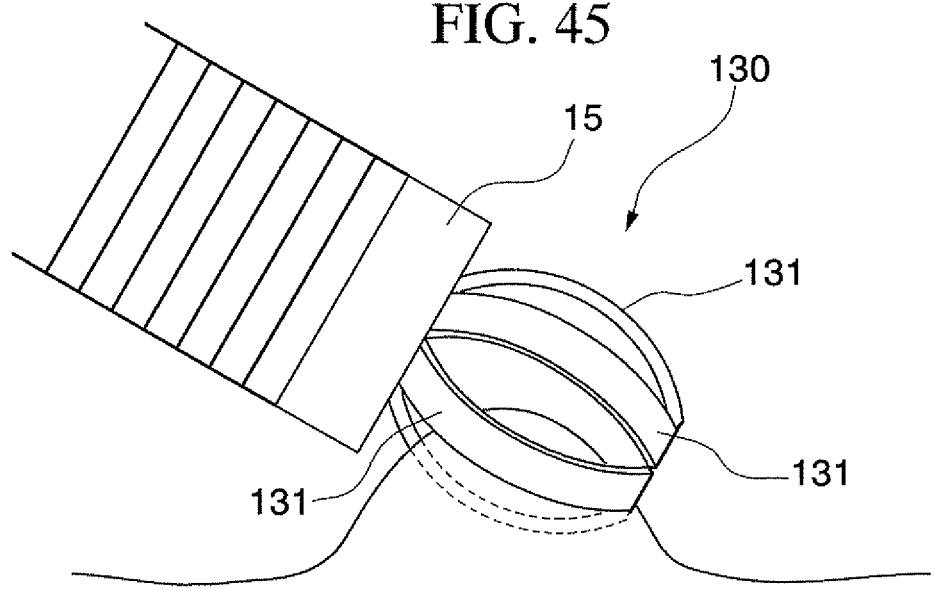
FIG. 45 is a perspective view explaining the operation of the grasper according to the sixth embodiment of the invention.

When a body tissue is ligatured, the respective grasping arms 131 are pressed against the body tissue in a state where they are opened. The slider of the operator main body is operated to retract the respective grasping arms 131 into the pressing ring (not shown) 15. Then, as shown in FIG. 44, the grasping arms 131 are closed in such a manner that a body tissue T1 is interposed among the distal end portions 131A of the respective grasping arms 131. FIG. 44 shows a case where the clip 130 is approached to the body tissue T1 in a direction substantially perpendicular to the body tissue T1. On the contrary, in a case where the clip 130 is approached to the body tissue T1 in a direction oblique with or substantially parallel to the body tissue T1, the body tissue T1 is interposed between the adjacent grasping arms 131 so as to be ligatured, as shown in FIG. 45.

In this clip 130, the body tissue T1 can be ligatured by the plurality of grasping arms 131. When the clip 130 is mounted towards the body tissue T1 in a direction oblique with or substantially parallel to the body tissue T1, the body tissue T1 can be interposed between the abdomen portions of the adjacent gasping claws 131 which swell further than the introduction tube 1. Therefore, the tissue T1 can be reliably ligatured regardless of the direction of the clip 130.

Figure 46:
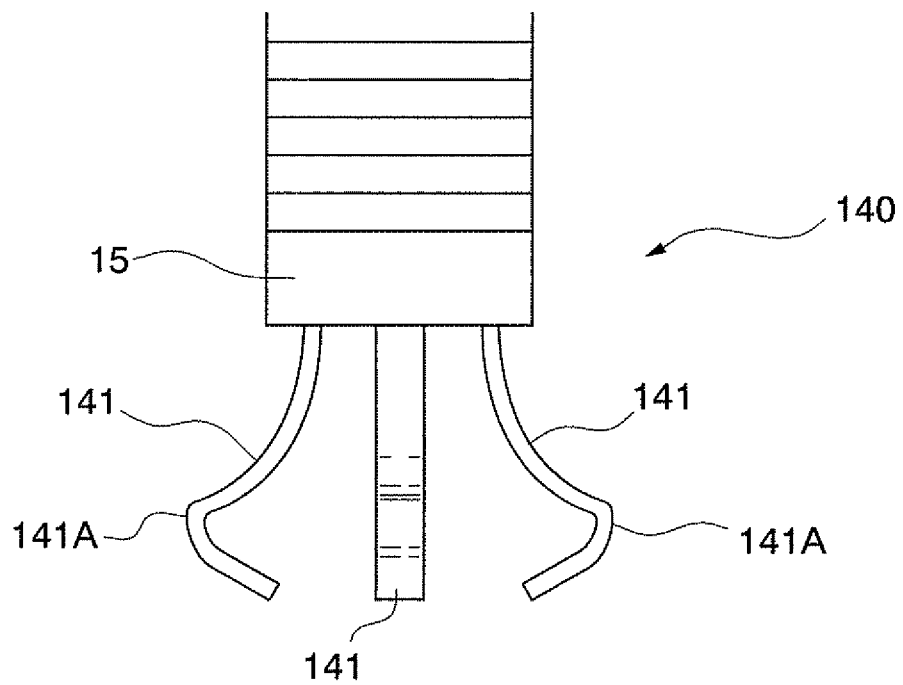
FIG. 46 is a perspective view of a grasper according to a modification of the sixth embodiment of the invention.

FIG. 46 is a diagram showing a modification of the sixth embodiment.

As shown in FIG. 46, a clip 140 has a plurality of grasping arms 141 of which each has a acute-angled bent portion 141A which is pulled outward. As such, when the grasping arms 141 have a portion projecting outward further than the diameter of the introduction tube 1, the same effect as the above-described embodiment can be obtained.

According to the sixth embodiment of the invention, since the body tissue T1 is ligatured by the plurality of grasping arms, the ligature is reliably performed. Further, regardless of the direction of the grasping tool such as the clip, the body tissue can be reliably ligatured.

The technical scope of the present invention is not limited to the above-described embodiments, but various changes and modifications in form and detail may be made therein without departing from the scope of the invention.

For example, in the above-described embodiments, the clip which is detachably attached to the distal end portion of the introduction tube and is held in the body after being operated to grasp a body tissue has been exemplified as a grasping tool. Without being limited thereto, however, the present invention can be applied to grasping forceps which are attached to the distal end of the coil sheath so as to be opened and closed.

Further, in the above-described embodiments, the operational elongate body composed of the operational wire and the suction conduit is used to operate the grasping arms in a direction where they are closed. Without being limited thereto, however, the grasping arms may be operated by the introduction tube in a direction where they are closed. That is, the grasping arms may be operated by the relative movement between the operational elongate body and the introduction tube in a direction where the grasping arms are closed.

The present invention relates to a grasper including an introduction tube that is capable of being inserted into a body cavity; an operational elongate body that is inserted into the introduction tube so as to advance and retract; and a grasping tool that is attached to a distal end portion of the introduction tube and is operated by the relative movement between the operational elongate body and the introduction tube so as to grasp a body tissue. The grasping tool has a plurality of grasping arms which are operated to be moved by the operational elongate body or the introduction tube, at least in a direction where the grasping arms are closed, so as to grasp the body tissue; and a retracting portion which retracts a portion of the body tissue between the plurality of grasping arms. According to the present invention, it is possible to accurately grasp a predetermined portion of a body tissue by using the grasping arms. According to the invention, a predetermined portion of a body tissue can be accurately grasped by the grasping arms.

What is claimed is:

1. A grasper comprising:
an introduction tube that is capable of being inserted into a body cavity;
an operational elongate body that is inserted into the introduction tube so as to advance and retract;
a grasping tool that is attached to a distal end portion of the introduction tube and is operated by a relative movement between the operational elongate body and the introduction tube so as to grasp a body tissue,
wherein the grasping tool further comprises:
a plurality of grasping arms which are indwellable inside of a patient's body;
a retracting portion in which a proximal end is connected to the operational elongate body, and the retracting portion retracts a portion of the body tissue between the plurality of grasping arms; and
a pressing ring which is fitted into an outer circumference of the plurality of grasping arms, and as the plurality of grasping arms are moved toward a proximal end side, the pressing ring moves toward a distal end side with respect to the moved plurality of grasping arms, and
wherein when the retracting portion is operated to be moved more than a predetermined distance in a proximal direction by operating the operational elongate body, the plurality of grasping arms are closed so as to grasp the body tissue:
the retracting portion has a locking portion at a distal end of the retracting portion, the locking portion is lockable to a portion of the body tissue so as to retract a portion of the body tissue between the plurality of grasping arms,
the locking portion is disposed so as to be relatively moved with respect to the plurality of grasping arms along a central axial line of the grasping arms and is operated to be moved with respect to the grasping arms by the operational elongate body,
when the locking portion is operated to be moved more than a predetermined distance toward the proximal end by the operational elongate body, the plurality of grasping arms are closed with a movement of the locking portion so as to grasp the body tissue such that the locking portion is locked to the grasping arms when the locking portion is moved by the predetermined distance, and such that when the locking portion is moved more than the predetermined distance, the grasping arms are moved toward the proximal end integrally with the locking portion, and the grasping arms being predisposed to spread out are inwardly pressed by the pressing ring so as to be closed.

2. The grasper according to claim 1, wherein the grasping tool is detachably attached to the distal end portion of the introduction tube and is indwellable in the body after being operated by the relative movement between the operational elongate body and the introduction tube so as to grasp the body tissue.

3. The grasper according to claim 1 or 2, wherein the retracting portion retracts a portion of the body tissue between the plurality of grasping arms through air suction.

4. The grasper according to claim 3, wherein the retracting portion has a suction tube which communicates with the inside of the introduction tube and suctions so as to retract the portion of the body tissue from a distal end opening thereof by suctioning the air from a proximal end side of the introduction tube.

5. The grasper according to claim 4, wherein the suction tube is disposed so as to be moved with respect to the plurality of grasping arms along the central axial line of the grasping arms and is operated to be moved with respect to the grasping arms by the operational elongate body, and
when the suction tube is operated to be moved more than the predetermined distance toward the proximal end by the operational elongate body, the plurality of grasping arms are closed with a movement of the suction tube so as to grasp the body tissue.

6. The grasper according to claim 5, wherein when the suction tube is operated to be moved more than the predetermined distance toward the proximal end by the operational elongate body, the suction tube is locked to the grasping arms when the suction tube is moved the predetermined distance, and
when the suction tube is moved more than the predetermined distance, the grasping arms are moved toward the proximal end integrally with the suction tube, and are inwardly pressed by the pressing ring disposed at the distal end portion of the introduction tube so as to be closed, the grasping arms being predisposed to spread out.

7. The grasper according to claim 3, wherein the operational elongate body is a suction conduit forming an air suction passage which is inserted into the introduction tube so as to advance and retract.

8. The grasper according to claim 3, where the retracting portion is formed integrally with the grasping arms and sucks the air from an suction opening which is formed on the inner side surface of at least one grasping claw among the plurality of grasping arms.

9. The grasper according to claim 3, wherein the retracting portion has a film which is disposed around the plurality of grasping arms or between the plurality of grasping arms.

10. The grasper according to claim 1 or 2, wherein the retracting portion has an adhesion portion which is attached to a portion of the body tissue by imparting energy to the portion of the body tissue and then retracts the portion of the body tissue between the plurality of grasping arms.

11. The grasper according to claim 10, wherein the adhesive portion is disposed so as to be moved with respect to the plurality of grasping arms along the central axial line of the grasping arms and is operated to be relatively moved with respect to the grasping arms by the operational elongate body, and
when the adhesive portion is operated to be moved more than the predetermined distance toward the proximal end by the operational elongate body, the plurality of grasping arms are closed in conjunction with the movement of the adhesive portion so as to grasp the body tissue.

12. The grasper according to claim 11, wherein when the adhesive portion is operated to be moved more than the predetermined distance toward the proximal end by the operational elongate body, the adhesive portion is locked to the grasping arms when the adhesive portion is moved the predetermined distance, and
when the adhesive portion is moved more than the predetermined distance, the grasping arms are moved toward the proximal end integrally with the adhesive portion, and are inwardly pressed by a pressing ring disposed at the distal end portion of the introduction tube so as to be closed, the grasping arms being predisposed to spread out.

13. The grasper according to claim 1 or 2, wherein the operational elongate body is an operational wire which is inserted into the introduction tube so as to advance and retract.

14. The grasper according to claim 1, wherein the retracting portion has a suction tube which communicates with the inside of the introduction tube and sucks and retracts a portion of the body tissue from the distal end opening thereof by suctioning the air from the proximal end side of the introduction tube.

15. The grasper according to claim 1, wherein the locking portion is further provided with a screw-shaped needle having a sharp distal end and is disposed on a distal end side of a cylindrical retracting base.

* * * * *